(12) United States Patent
Kahook et al.

(10) Patent No.: US 10,945,883 B2
(45) Date of Patent: Mar. 16, 2021

(54) OCULAR IMPLANTS, INSERTER DEVICES, AND METHODS FOR INSERTION OF OCULAR IMPLANTS

(71) Applicant: NEW WORLD MEDICAL, INC., Rancho Cucamonga, CA (US)

(72) Inventors: Malik Y. Kahook, Denver, CO (US); Joey Tran, Ontario, CA (US); Patrick S. Chen, Hacienda Heights, CA (US); Eric Porteous, Corona, CA (US); Daniel R. Davis, Ontario, CA (US); Nathan R. Collins, Chino, CA (US); Nico J. Slabber, Eastvale, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 0 days.

(21) Appl. No.: 16/712,723

(22) Filed: Dec. 12, 2019

(65) Prior Publication Data
US 2020/0138629 A1    May 7, 2020

Related U.S. Application Data

(63) Continuation of application No. PCT/US2019/048926, filed on Aug. 29, 2017.
(Continued)

(51) Int. Cl.
*A61F 9/007* (2006.01)
*A61B 17/34* (2006.01)
*A61F 2/00* (2006.01)

(52) U.S. Cl.
CPC ...... *A61F 9/00781* (2013.01); *A61B 17/3468* (2013.01); *A61F 2002/0081* (2013.01);
(Continued)

(58) Field of Classification Search
CPC ........ A61F 19/00781; A61F 2002/0081; A61F 2210/0004; A61F 2220/0016;
(Continued)

(56) References Cited

U.S. PATENT DOCUMENTS

| 2004/0260227 A1* | 12/2004 | Lisk, Jr. | A61F 9/00781 604/8 |
| 2006/0116626 A1* | 6/2006 | Smedley | A61F 9/00781 604/8 |

(Continued)

FOREIGN PATENT DOCUMENTS

WO    WO-2010111528 A2    9/2010

OTHER PUBLICATIONS

International Search Report and Written Opinion for Application No. PCT/US2019/048926, dated Jan. 29, 2020, 20 pages.

*Primary Examiner* — Andrew J Mensh
(74) *Attorney, Agent, or Firm* — Morgan, Lewis & Bockius LLP

(57) ABSTRACT

Intraocular drainage devices, intraocular implantation procedures, and inserter devices for intraocular implantation procedures are disclosure. A disclosed intraocular drainage device includes a tube having a distal end and a body disposed proximal to the tube. An inlet port is disposed on the distal end of the tube and configured to receive an influent fluid from an anterior chamber of an eye. An inlet fluid pathway is coupled to the inlet port and extends at least partially through the tube. A plurality of outlet fluid pathways extend at least partially through the body and branch from the inlet fluid pathway. A plurality of outlet ports are disposed on the body and coupled to the plurality of outlet fluid pathways. A disclosed inserter device for an ocular implantation procedure includes a handle, a needle, and a plunger. The needle is disposed on a distal end of the handle and configured to hold an intraocular drainage device. The
(Continued)

plunger is coupled to the needle and disposed in the handle. The plunger is disposed distal to a vacuum chamber within the handle and configured to retract the needle based on a proximal force applied by the vacuum chamber.

18 Claims, 31 Drawing Sheets

Related U.S. Application Data

(60) Provisional application No. 62/734,216, filed on Sep. 20, 2018, provisional application No. 62/734,213, filed on Sep. 20, 2018, provisional application No. 62/726,117, filed on Aug. 31, 2018.

(52) U.S. Cl.
CPC ........... *A61F 2210/0004* (2013.01); *A61F 2220/0016* (2013.01); *A61F 2240/001* (2013.01); *A61F 2250/0013* (2013.01); *A61F 2250/0036* (2013.01)

(58) Field of Classification Search
CPC ........ A61F 2240/001; A61F 2250/0013; A61F 2250/0036; A61B 17/3468
USPC .............................................. 604/8
See application file for complete search history.

(56) References Cited

U.S. PATENT DOCUMENTS

| | | | |
|---|---|---|---|
| 2010/0249691 A1* | 9/2010 | Van Der Mooren | A61F 9/00781 604/9 |
| 2010/0274259 A1* | 10/2010 | Yaron | A61F 9/00781 606/108 |
| 2013/0096514 A1* | 4/2013 | Lareau | A61M 39/24 604/246 |
| 2014/0163448 A1* | 6/2014 | Lind | A61F 9/00781 604/9 |
| 2014/0243729 A1* | 8/2014 | Rynerson | A61F 9/00781 604/8 |
| 2016/0302919 A1* | 10/2016 | Scorsin | A61F 2/2412 |

* cited by examiner

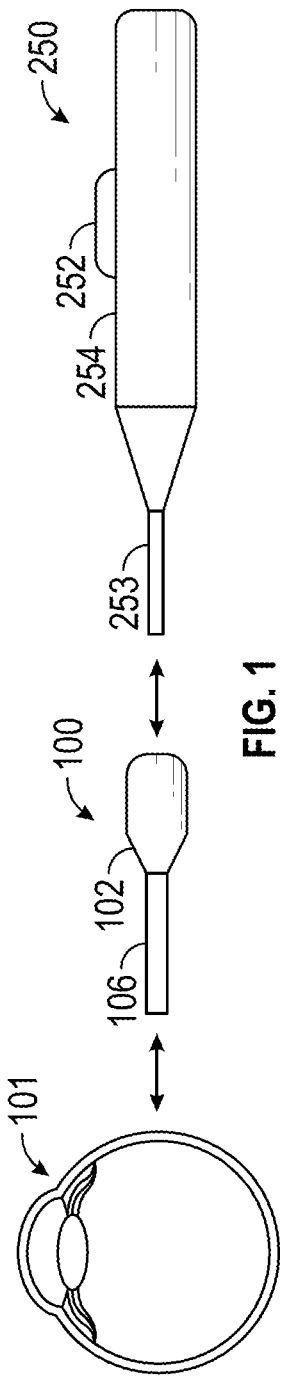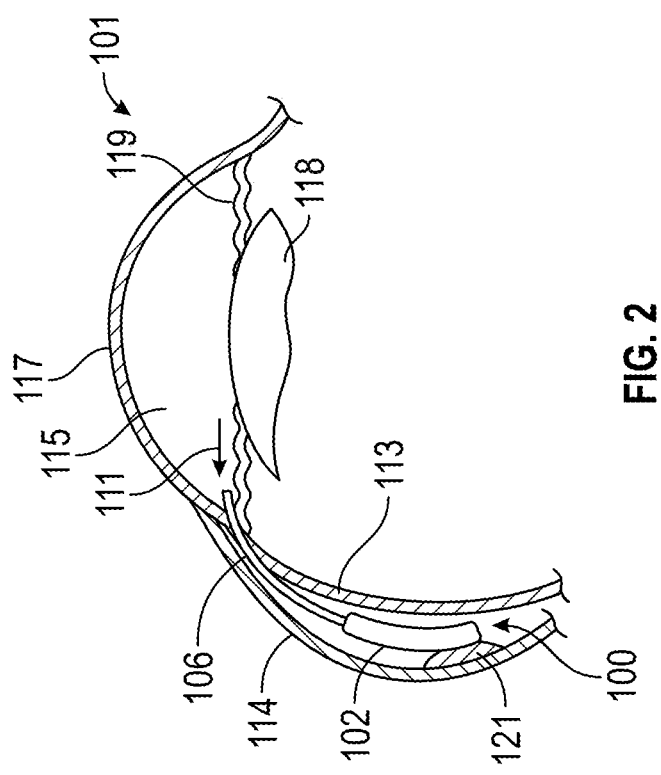
FIG. 1
FIG. 2

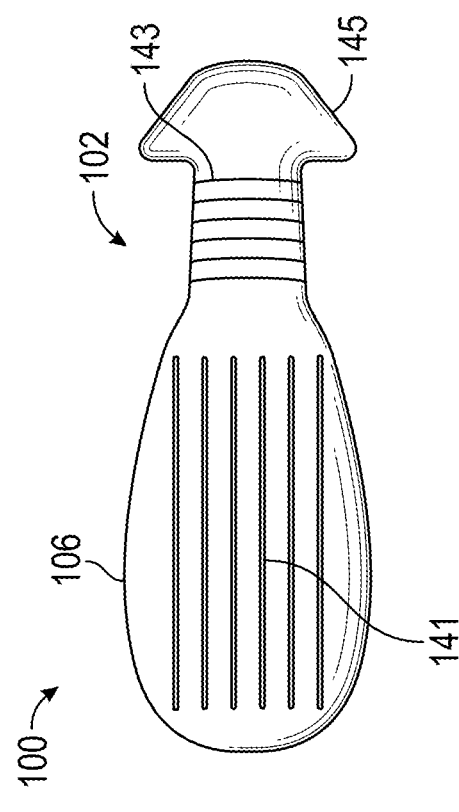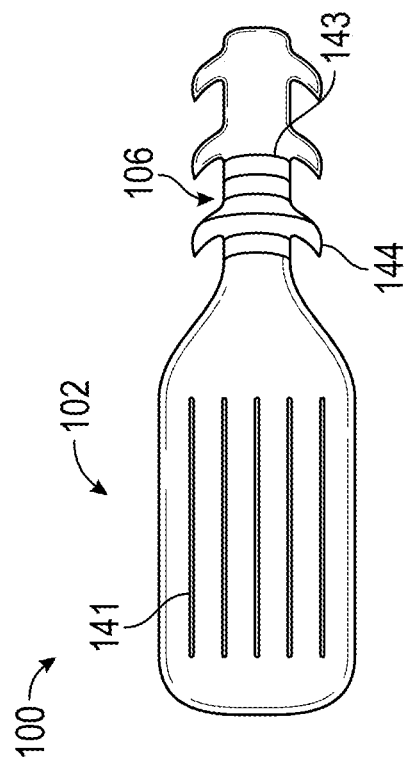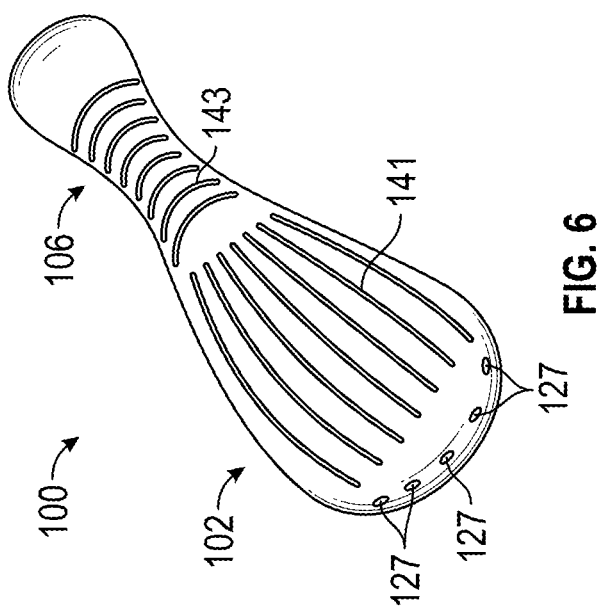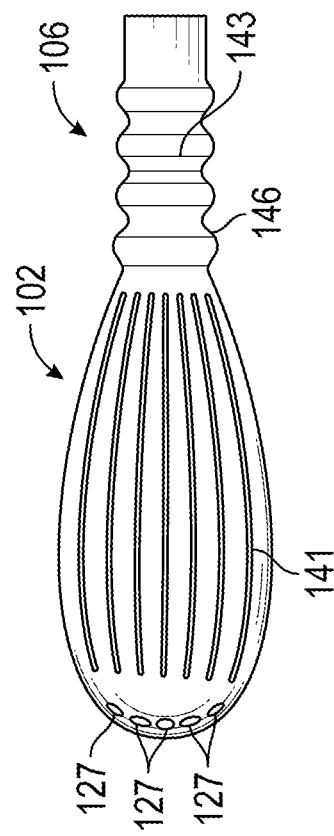

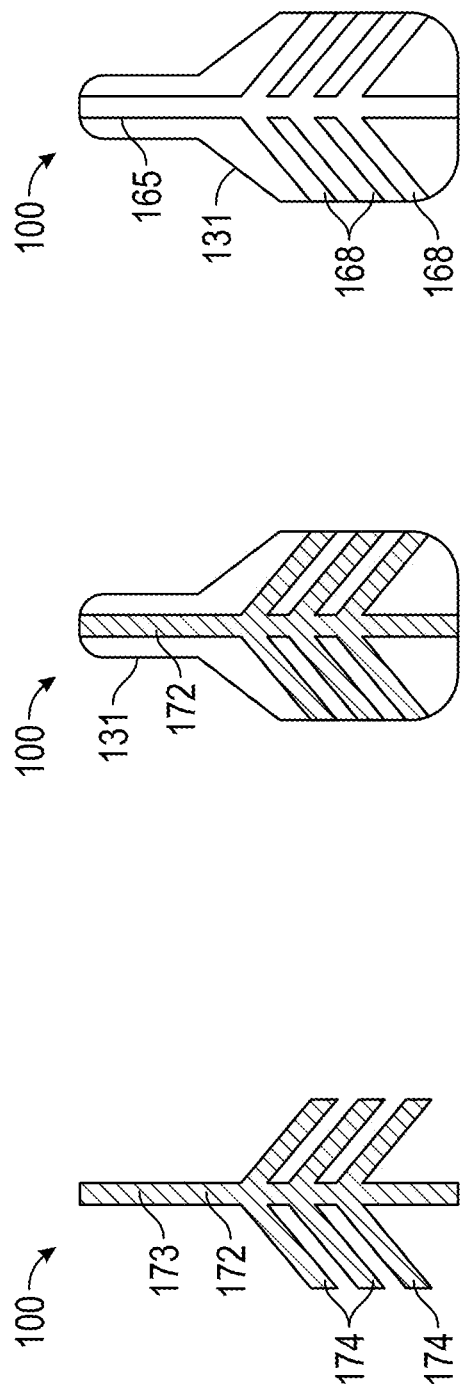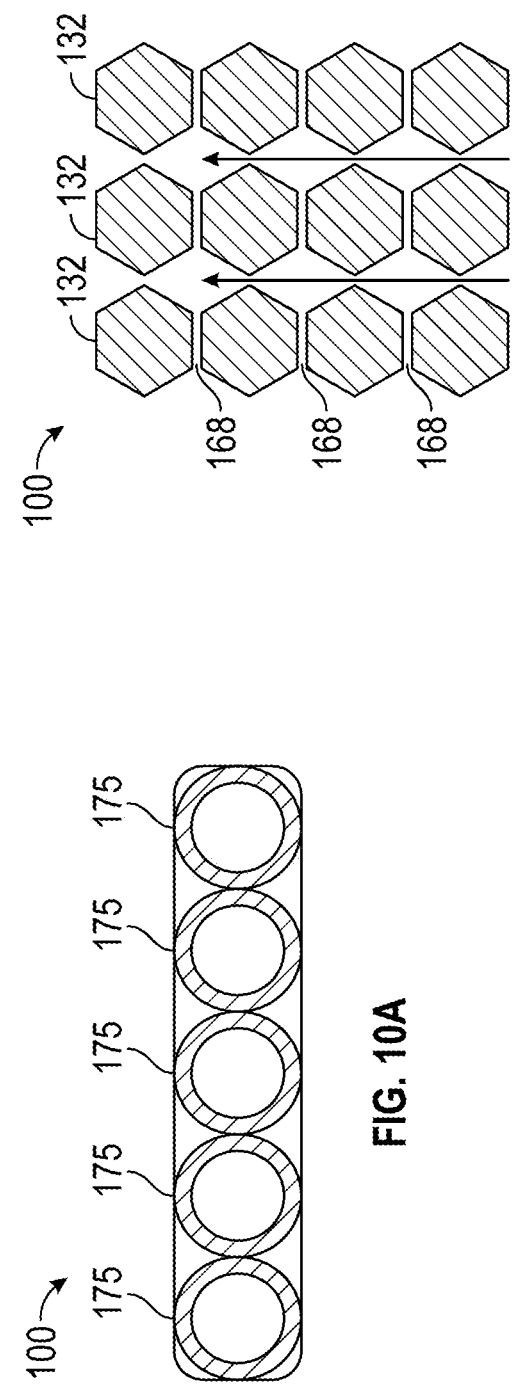

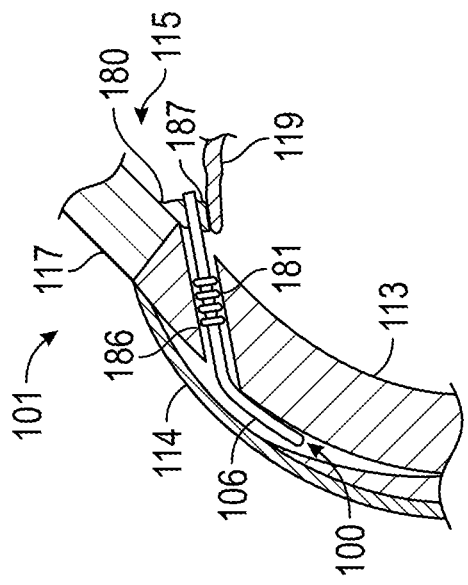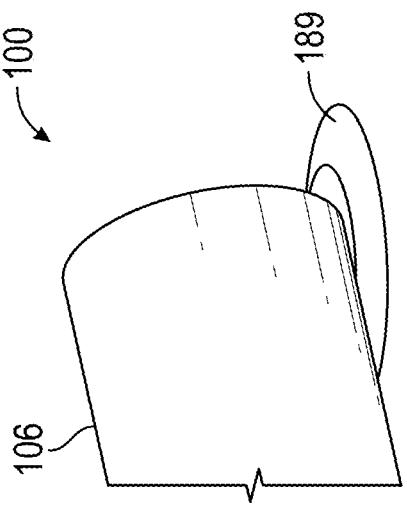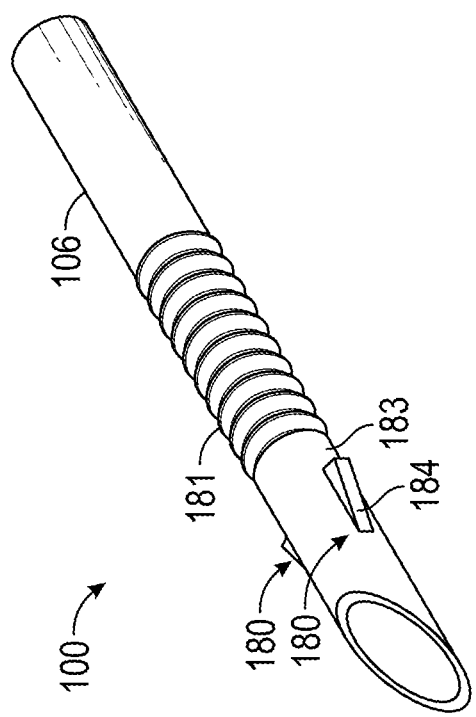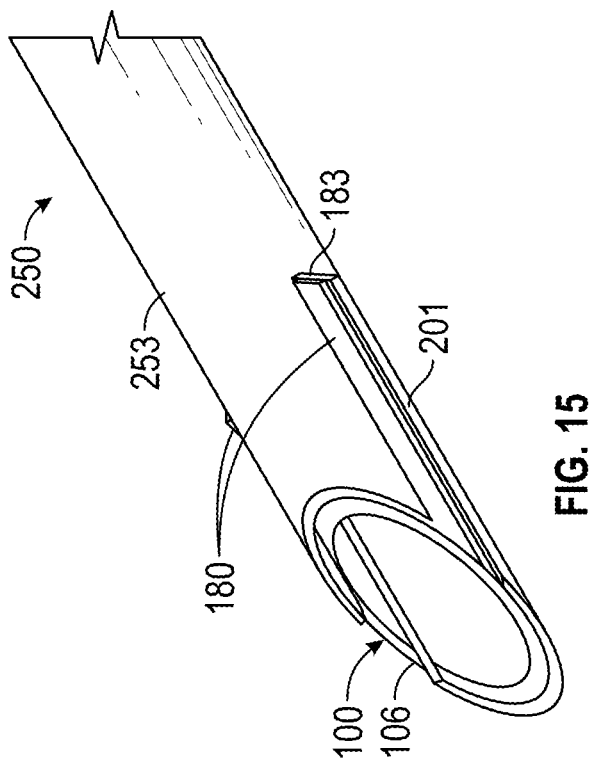

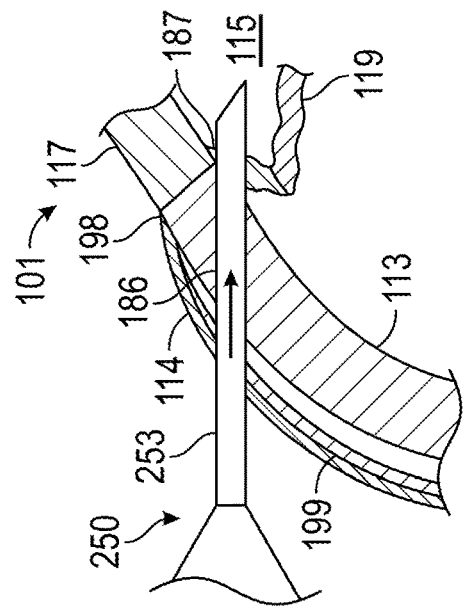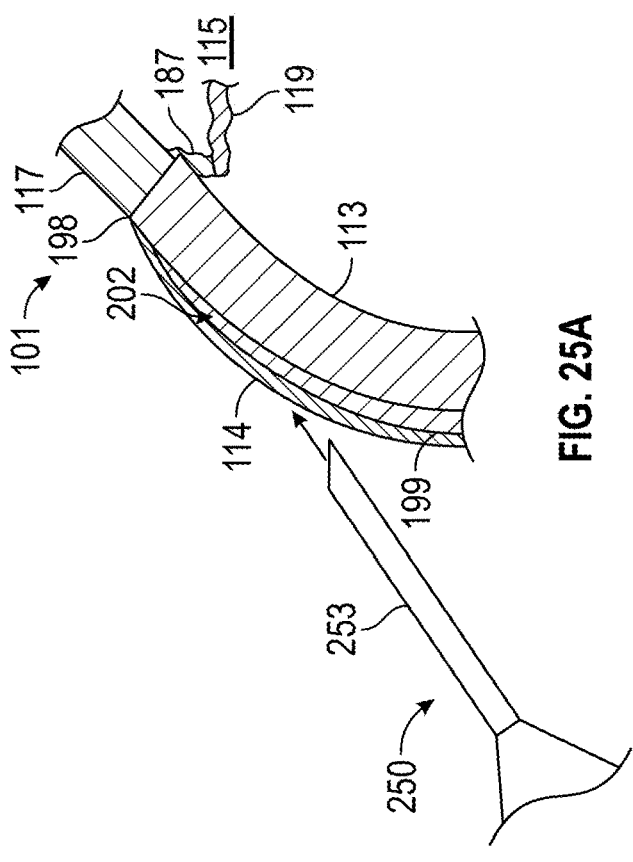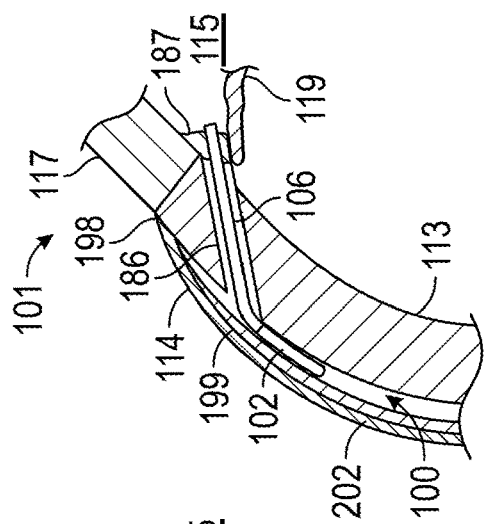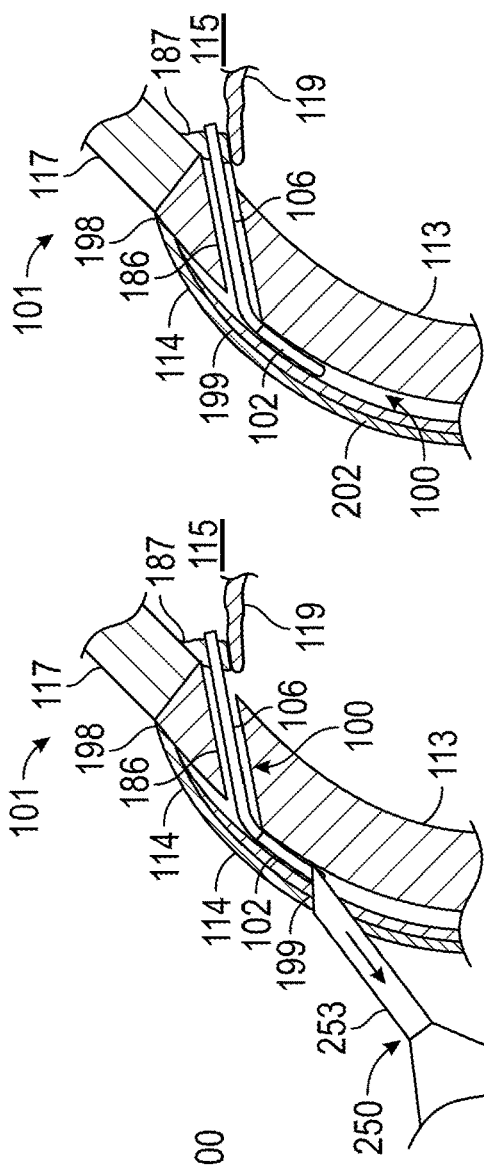
FIG. 25A
FIG. 25B
FIG. 25C
FIG. 25D
FIG. 25E

OCULAR IMPLANTS, INSERTER DEVICES, AND METHODS FOR INSERTION OF OCULAR IMPLANTS

CROSS-REFERENCE TO RELATED APPLICATIONS

This application is a continuation of and claims priority to International Patent Application No. PCT/US2019/048926, entitled "OCULAR IMPLANTS, INSERTER DEVICES, AND METHODS FOR INSERTION OF OCULAR IMPLANTS," filed Aug. 29, 2019, which claims the benefit of priority under 35 U.S.C. § 119 from U.S. Provisional Application No. 62/734,216, entitled "INSERTER DEVICES AND METHODS FOR INSERTION OF OCULAR IMPLANTS," filed Sep. 20, 2018, U.S. Provisional Application No. 62/734,213, entitled "OCULAR IMPLANTS, INSERTER DEVICES, AND METHODS FOR INSERTION OF OCULAR IMPLANTS," filed Sep. 20, 2018, and U.S. Provisional Application No. 62/726,117, entitled "OCULAR IMPLANT," filed Aug. 31, 2018, the entirety of which are incorporated herein by reference.

BACKGROUND

Aqueous humour typically drains from the anterior chamber of the eye via the conventional (trabecular meshwork and canal of Schlemm) and unconventional (Uveoscleral) outflow pathways. However, in some circumstances, reduced drainage of aqueous humour can increase intraocular pressure (IOP) which can cause damage to the optic nerve. Accordingly, it would be desirable to be able to provide increased drainage of aqueous humour from the anterior chamber, particularly for glaucoma patients.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 1 is a schematic diagram of an intraocular implantation system, in accordance with some embodiments of the present disclosure.

FIG. 2 is a cross section view of an intraocular drainage device in situ in an eye of a patient, in accordance with some embodiments of the present disclosure.

FIG. 4 is a top view of an intraocular drainage device, in accordance with some embodiments of the present disclosure.

FIG. 5 is a top view of an intraocular drainage device, in accordance with some embodiments of the present disclosure.

FIG. 6 is a three-dimensional view of an intraocular drainage device, in accordance with some embodiments of the present disclosure.

FIG. 7 is a top view of an intraocular drainage device, in accordance with some embodiments of the present disclosure.

FIGS. 9A-9C are diagrams showing a method of making an intraocular drainage device, in accordance with some embodiments of the present disclosure.

FIG. 10A is a cross section view of an intraocular drainage device, in accordance with some embodiments of the present disclosure.

FIG. 10B is a top view of an intraocular drainage device, in accordance with some embodiments of the present disclosure.

FIG. 13 is a three-dimensional view of an intraocular drainage device, in accordance with some embodiments of the present disclosure.

FIG. 14 is a cross section view of an intraocular drainage device in situ in an eye of a patient, in accordance with some embodiments of the present disclosure. view of an FIG. 15 is a three-dimensional view of an intraocular drainage device disposed in an inserter device, in accordance with some embodiments of the present disclosure.

FIG. 16 is a three-dimensional view of an intraocular drainage device, in accordance with some embodiments of the present disclosure.

FIGS. 25A-25E are cross section views of an implantation procedure using an inserter device, in accordance with some embodiments of the present disclosure.

FIGS. 29A-29C are schematic views an inserter device during an implantation procedure, in accordance with some embodiments of the present disclosure.

DETAILED DESCRIPTION

Figure 3:
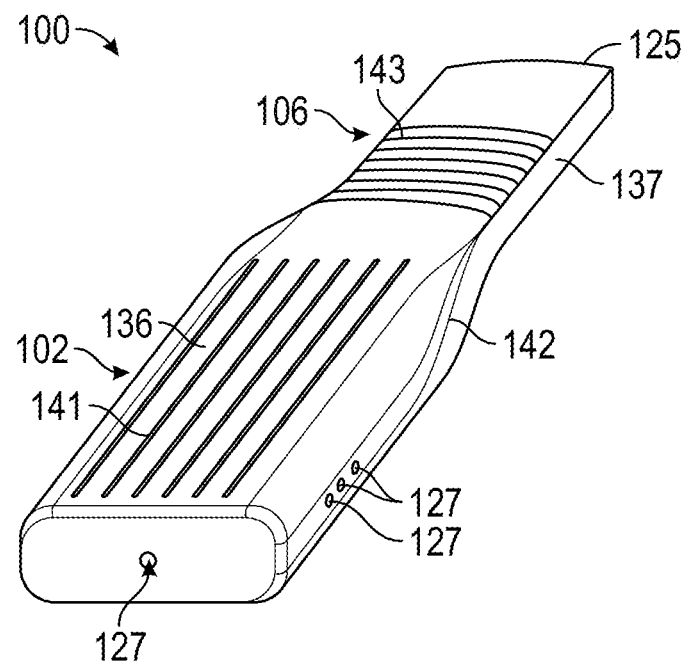
FIG. 3 is a three-dimensional view of an intraocular drainage device, in accordance with some embodiments of the present disclosure.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Intraocular Implantation System

According to some embodiments, for example as shown in FIG. 1, an inserter device 250 can be used to implant an intraocular drainage device 100 into a patient's eye 101.

As shown in FIG. 1, for example, a medical or surgical instrument such as the inserter device 250 may include a handle 254 configured to be gripped by a surgeon's hand or other operator, and an actuator 252, disposed on the handle 254 and configured to actuate an internal mechanism within inserter device 250 to release intraocular drainage device 100 from the distal end of the inserter device 250. The distal end of the inserter device 250 can include a needle 253, which may be configured to pierce tissue of the eye 101 and/or house the drainage device 100 prior to release.

The actuator 252 can be implemented as any suitable mechanism that permits the operator to manipulate the actuator and release the drainage device 100. The actuator 252 can, for example, include a push button, a slider, a twist sleeve, an electronic touch sensitive button, and/or any other suitable component that can be manipulated by an operator to actuate an internal mechanism within the inserter device 250. Upon actuation by actuator 252, the internal mechanism can be configured to release the drainage device 100 by pushing the drainage device 100 distally out of the needle 253 and/or by retracting the needle 253 or another sleeve proximally around the drainage device 100 to leave the drainage device 100 in place in the intended target site (e.g., intraocular site within the patient's eye 101).

According to some embodiments, for example as shown in FIG. 1, an intraocular device such as an intraocular drainage device 100 may include a body 102 and a tube 106. The tube 106 may have a lumen, and as shown in FIG. 1, the tube 106 can have a proximal end which is configured to be coupled to the body 102. The tube 106 can, for example, be integrally formed as a single piece with the body 102, or the tube 106 can be manufactured as a separate piece that is inserted into or otherwise attached to the body 102 (e.g., at a distal end of the body 102) to provide a fluid coupling to the body 102. A distal end of the tube 106 can be inserted into an internal chamber of a patient (e.g., an anterior chamber of the eye 101) to provide a fluid coupling to the internal chamber. The tube 106 may be implemented as an input tube with a flow path for influent flow (e.g., a flow path into the distal end of the tube 106). Although examples are described herein where drainage device 100 includes both a tube 106 and a body 102, other embodiments are contemplated in which the drainage device 100 includes only a tube 106 or only a body 102.

According to some embodiments, components of the drainage device 100 such as the body 102 and/or tube 106 may be flexible and made from a biocompatible flexible material such as silicone and/or hydrophilic or hydrophobic acrylic. Additionally or alternatively, it is contemplated that any of a variety of other materials can be suitable. Further, although examples are described herein in which body 102 and tube 106 are flexible and made from flexible biocompatible materials, other implementations with rigid materials are contemplated.

According to some embodiments, the tube 106 and/or the body 102 can include features to reduce a risk of hypotony (intraocular pressure that is low, increasing likelihood for ocular complications that can occur due to excess aqueous drainage). For example, the tube 106 and/or body 102 can include a valve, a flow restricting lumen, and/or other mechanisms to reduce a risk of hypotony.

According to some embodiments, for example as shown in FIG. 2, the drainage device 100 may be surgically implanted between the sclera 113 and conjunctiva 114 of the eye 101 of a patient to provide an aqueous shunt that may, for example, reduce IOP for treatment of glaucoma or other conditions. According to some embodiments, the drainage device 100 may be implanted into the anterior chamber 115 of the eye 101 using the inserter device 250 and using an ab externo procedure. For example, during implantation the needle 253 may be inserted through the sclera 113 to form a scleral tract, and the distal tip of the s 253 may be inserted into the anterior chamber 115 from through the sclera 113. The actuator 252 may then be manipulated to retract the needle or otherwise release the drainage device 100 and to leave portions of the drainage device 100 implanted within the scleral tract. After the inserter device 250 is removed, a portion of the implanted tube 106 may extend through the scleral tract and connect the anterior chamber 115 to a conjunctival or sub-Tenon's pocket. The drainage device 100 may be implanted such that aqueous humour or other fluid flows through device 100 (e.g., in a fluid flow direction as indicated by arrow 111) and out from one or more outlet ports to be absorbed the surrounding tissue (e.g., via the epi-scleral venous system). In other embodiments, the device may be implanted through an ab interno approach which involves accessing the anterior chamber through a clear corneal incision, advancing the needle to the appropriate quadrant, piercing the angle near the scleral spur and advancing the introducer (e.g., inserter device 250) into the sub-Tenon's space prior to retracting the introducer and leaving the drainage device in place to drain fluid from the anterior chamber to the sub-Tenon's space. Similar approaches may be used from an ab-interno or ab-externo approach to deposit the drainage device in the suprachoroidal space or to connect one eye compartment to another or one eye compartment to an extraocular space including a transconjunctival, translimbal or transcorneal outflow pathway.

FIG. 2 schematically shows a cross-sectional view of intraocular drainage device 100 disposed in situ in a patient's eye 101 such that body 102 is disposed between the sclera 113 and conjunctiva 114 of the patient's eye. The region between the sclera 113 and conjunctiva 114 can form a conjunctival pocket for retaining body portion 102 of the drainage device. According to some embodiments, the body 102 may be implanted into a sub-Tenon's space between the sclera 113 and the conjunctiva 114. As shown, tube 106 may extend through sclera 113 so that aqueous humour in the anterior chamber 115 of the eye (bounded in part by cornea 117, lens 118, and iris 119) can flow into the lumen of tube 106 (as indicated by arrow 111). As shown in FIG. 2, fluid that has flowed through the device 100 may form a bleb 121 on and/or around device 100 that can be absorbed into the patient's tissue. In this way, excess fluid pressure in anterior chamber 115 associated with a glaucoma condition may be relieved.

Drainage Device

According to some embodiments, for example as shown in FIG. 3, a drainage device 100 can have an inlet port 125 and a plurality of outlet ports 127. The inlet port 125 can be configured to receive influent fluid, such as influent aqueous humour from an anterior chamber of an eye, while the outlet ports 127 can be configured to discharge an effluent fluid, such as effluent aqueous humour into a bleb or other patient tissue. The inlet port 125 can, for example, be disposed at a distal end of tube 106 and be configured to contact an anterior chamber to receive aqueous humour.

The drainage device 100 can be implemented as a manifold in which lumens or other fluid pathways (not visible in FIG. 3) can extend through the device 100 and fluidly connect the inlet port 125 to the various outlet ports 127. The ports and lumens can be configured so that the inlet port 125 connects to an inlet lumen that branches into multiple outlet lumens or other outlet fluid pathways that terminate at multiple redundant outlet ports 127. Each of the lumens may provide a substantially tubular fluid pathway extending at least partially through an interior of the drainage device 100. The use of multiple outlet ports and fluid pathways can, for example, provide various points of exit for the fluid in case any one or more of the outlet ports 127 becomes blocked (e.g., with patient tissue). The use of multiple outlet ports may also allow the fluid to flow into the sub-Tenon's space as well as sub-conjunctival space simultaneously. For example, the outlet ports 127 may be configured so that, when implanted in an eye, one or more of the outlet ports 127 contact or otherwise permit fluid flow into the sub-Tenon's space and one or more others of the outlet ports 127 contact or otherwise permit fluid flow into the sub-conjunctival space. According to some embodiments, the inlet lumen may provide a single influent channel for fluid flow to funnel through before reaching the multiple outlet lumens and outlet ports 127 so that the inlet lumen may provide a primary source of flow restriction for regulating IOP. However, in various embodiments the size number of outlet lumens may also dictate a pressure drop across the drainage device. According to some embodiments, for example, the inlet lumen may have a smaller diameter than one, several, or all of the outlet lumens to permit the inlet lumen to provide a primary restriction on fluid flow. However, other implementations are contemplated in which the inlet and outlet lumen(s) have any appropriate diameter that can be the same or different from each other in any suitable manner to permit the fluid to flow through the drainage device 100.

According to some embodiments, the inlet lumen can be oriented in a transverse direction to one, several, or all of the outlet lumens connected to the outlet ports. For example, one, several, or all of the outlet lumens may be oriented within a range of between about 90 degrees (perpendicular) and 45 degrees relative to the direction of the input lumen with reference to the direction of fluid flow. An example of such a 45 degree arrangement is also shown in FIGS. 9A-9C discussed below. Although examples of orientations are described, other implementations are contemplated in which other angles and orientations may be used for the lumens or fluid pathways.

According to some embodiments, the outer surface of the body 102 can be coated with a biodegradable material, such as polyvinyl alcohol or poly(lactic-co-glycolic acid) (PLGA). The biodegradable material may be coated to cover the ports on the body such as all of the outlet ports 127 to provide an initial occlusion of the holes and prevent fluid flow through the device during an initial post-operative healing time period. Over time, the coating may degrade to expose the ports and other outer surface features and open up the fluid pathways to permit drainage of fluid through the drainage device 100 after the initial post-operative period has expired. In some embodiments, the PLGA or other biodegradable coating may contain anti-fibrotic or anti-inflammatory molecules such as steroids or rapamycin. In some embodiments, the lumen or lumens of the device are coated with hydrophilic material to encourage fluid transmission. In other embodiments, the lumen and/or the entire device is coated with heparin or other material to decrease clot formation in or on the device while in situ.

Although examples are described in which drainage device 100 includes multiple outlets, other implementations are contemplated in which only one outlet port or only one lumen is included.

According to some embodiments, for example as shown in FIG. 3, the body 102 can be disposed proximal to the tube 106 and expanded in size relative to the tube 106. The tube 106 can thus provide a neck region of the device 100 that is generally narrower than the body region 102 and disposed distal to the body 102. According to some embodiments, the inlet port 125 may be coupled to an inlet lumen that extends at least partially through the neck region in the distal portion of the device 100. Additionally or alternatively, the plurality of outlet ports 127 may be coupled to a plurality of outlet lumens or other outlet fluid pathways that each branch off of the inlet lumen and extend at least partially through the body 102 in the proximal portion of the device. Upon implantation, the body 102 can, for example, be retained in the conjunctival pocket and rest against surrounding tissue such as an outer surface of the sclera and/or inner surface of a conjunctiva.

According to some embodiments, for example as shown in FIG. 3, the body 102 can be implemented with a plate-like structure defining a minor axis and a major axis, both of which axes may be transverse to the longitudinal axis of the drainage device 100 defined by the direction of influent fluid flow at the inlet port 125. A size of the body 102 in a direction of the major axis may be made larger than a size of the body 102 in a direction of the minor axis to result in a plate-like structure that may facilitate bleb formation in the conjunctival pocket. Upon implantation, the body 102 may rest in the pocket such that the major axis extends transverse to the surface of the sclera while the minor axis extends normal to the scleral surface. However, other implementations are contemplated in which the body 102 does not have a plate-like structure. For example, the body 102 can have any other suitable shape or size that can be expanded relative to the tube 106, with a larger outer diameter or outer circumference than the outer diameter or outer circumference of the tube 106.

According to some embodiments, an outer surface of the body 102 can include a top surface 136 and a bottom surface (not visible in FIG. 3) opposite to the top surface. A sidewall surface 137 may be disposed between the top and bottom surfaces. According to some embodiments, the bottom surface can, for example, be made concave and face the scleral surface so that the concave shape conforms to the convex shape of the sclera surface. The top surface 136 can, for example, be made convex and face the conjunctiva so that the convex surface conforms to the concave interior shape of the conjunctiva surface. Other implementations are contemplated in which the top and/or bottom surfaces can be made flat or have other contoured geometries.

According to some embodiments, for example as shown in FIG. 3, the outlet ports 127 can be distributed along the sidewall surface 137 and a proximal end of the body 102. Although examples are described in which outlet ports are distributed along the sidewall and/or distal end of the body 102, other implementations are contemplated in which the outlet ports 127 can generally be disposed on any one or more of the top surface 136, bottom surface, sidewall surface(s) 137, and/or proximal surface at the proximal end of the device 100. According to some embodiments, the outlet ports 127 can be distributed across multiple locations on the outer surface of the device 100 to reduce a likelihood of a localized obstruction blocking all of the outlet ports 127.

According to some embodiments, for example as shown in FIG. 3, the outer surface can include grooves such as microgrooves 141, microgrooves 142, and/or microgrooves 143. As shown in FIG. 3, the microgrooves 141 can be disposed in the body 102 and extend along the outer top surface 136 and/or bottom surface. The microgrooves 142 can be disposed in the body 102 and extend along the sidewall surface 137. Some or all of the microgrooves can, for example, extend in regions between the outlet ports 127, such as microgrooves 142 shown in FIG. 3. As shown in FIG. 3, the microgrooves 141 and/or microgrooves 142 can extend substantially parallel to each other in a longitudinal direction that may be substantially the same as the direction of influent fluid flow. The microgroove patterns 141 and/or 142 may, for example, aid in the healing response of the eye and/or improve the functioning of the device over time following implantation. For example, in some embodiments surface patterning including grooves such as microgrooves 141 and 142 can be used to enhance, or prevent, cell or bacterial attachment to the implanted device. Additionally or alternatively, microgroove patterns may be provided to help organize cells into a controlled alignment along the implant. In the example shown, only a few microgrooves are shown for illustrative purposes. However, in various implementations, one, two, three, four, tens, hundreds, or thousands of microgrooves may be formed, for example, to substantially cover a surface such as top surface 136, bottom surface, sidewall surface 137, and/or any other desired surface.

As shown in FIG. 3, microgrooves 143 may be included in a neck region and disposed distal to the microgrooves 141 and/or microgrooves 142 in the body region 102. The microgrooves 143 may extend substantially perpendicular to the microgrooves 141 and/or microgrooves 142. For example, the microgrooves 143 may extend circumferentially around the tube 106, in a direction substantially perpendicular to the direction of fluid flow, while the microgrooves 141 and/or 142 may extend longitudinally along the body 102 substantially parallel to the direction of fluid flow. According to some embodiments, the perpendicular microgrooves 143 may be implemented as retention features that facilitate retention of the device and minimize migration of the device upon implantation to the intraocular site. In some embodiments, the perpendicular microgrooves 143 may be relatively larger than the microgrooves 141 and/or 142. For example, each microgroove or microgroove pattern may be formed in equally-spaced rows. Each microgroove may have a width, a depth, and a separation from an adjacent microgroove. According to some embodiments, each of the microgrooves 141 and/or 142 may have a width, a depth, and/or a separation from an adjacent microgroove ranging from between about 10 and 40 microns (e.g., each equal to about 25 microns in one implementation). By contrast, each of the microgrooves 143 may have a width, a depth, and a separation greater than about 40 microns, such as in the range of between about one to two orders of magnitude greater than the microgrooves 141 and/or 142 (e.g., equal to about 635 microns in one implementation). It should be understood that while examples are described with respect to particular dimensions, other implementations are contemplated in which the dimensions fall outside of these ranges. According to some embodiments, microgroove patterns may be formed by laser patterning the surface of the drainage device 100 or by any other suitable method to create surface patterns.

According to some embodiments, for example as shown in FIGS. 4-7, drainage device 100 such as tube 106 of drainage device may include one or more retention features instead of or in addition to circumferential microgrooves 143. The retention features may, for example, facilitate retention of the drainage device 100 in the implantation site and/or minimize migration of the drainage device 100 without a need for sutures.

According to some embodiments, for example as shown in FIG. 4, one or a plurality of retention fins 144 may be included in a tube region 106 of drainage device 100. As shown in FIG. 4, the retention fins 144 may be implemented as barbs angled towards a proximal end of the body 102. The proximal orientation may facilitate insertion distally into or between patient tissue. Additionally or alternatively, the proximally angled orientation may serve to reduce a tendency of the implanted device to migrate proximally in a manner that could remove the drainage device 100 from the anterior chamber after implantation.

According to some embodiments, for example as shown in FIG. 5, a distal end of tube 106 may include an orifice fitting 145 to facilitate retention of the device 100. The distal end of the orifical fitting 145 may include a portion flared radially outward to facilitate retention when the distal end is inserted into the anterior chamber of the eye.

According to some embodiments, for example as shown in FIG. 6, the body 102 may include contoured profile such as an hourglass shape. The hourglass shape may include a neck region in which portions of the device 100 on opposing ends of the neck region are expanded outward or have increased diameter compared to the relatively narrow neck region. For example, not only may body 102 have a larger size than the neck region, but a distal tip of the tube 106 on an opposite side of the neck region may also have a larger size than neck and be expanded relative to the neck. According to some embodiments, for example as shown in FIG. 6, the expanded distal tip of the tube 106 may be smaller (e.g., in diameter or cross sectional area) than the largest portion of the body 102 on the opposing side of the neck.

According to some embodiments, for example as shown in FIG. 7, the tube 106 may include retention bumps 146 to facilitate retention of the implanted body.

Figure 8A:
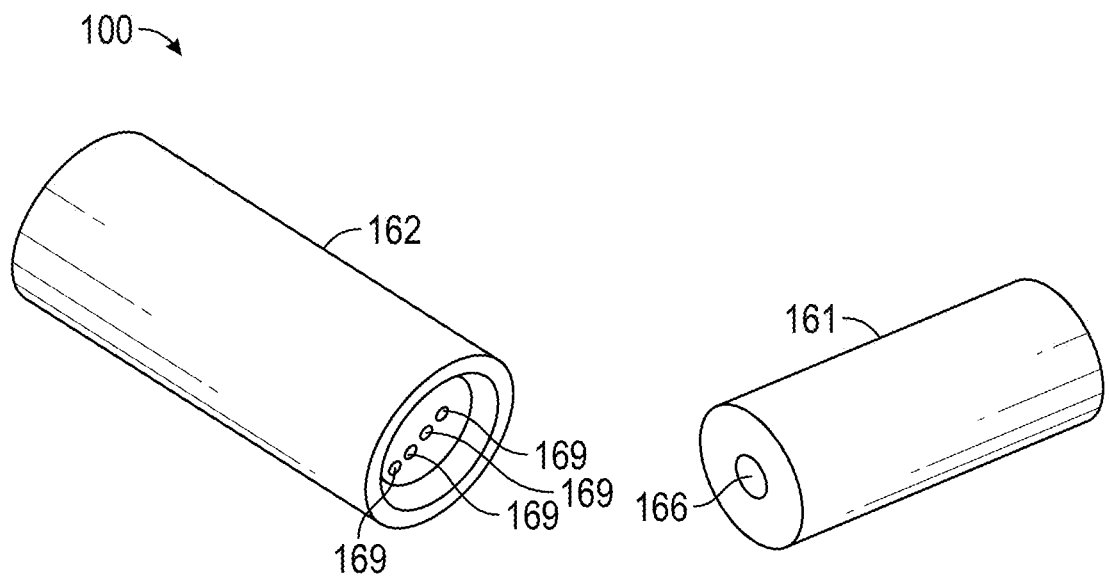
FIGS. 8A-8B are diagrams showing a two piece construction and method of making an intraocular drainage device, in accordance with some embodiments of the present disclosure.
Figure 8B:
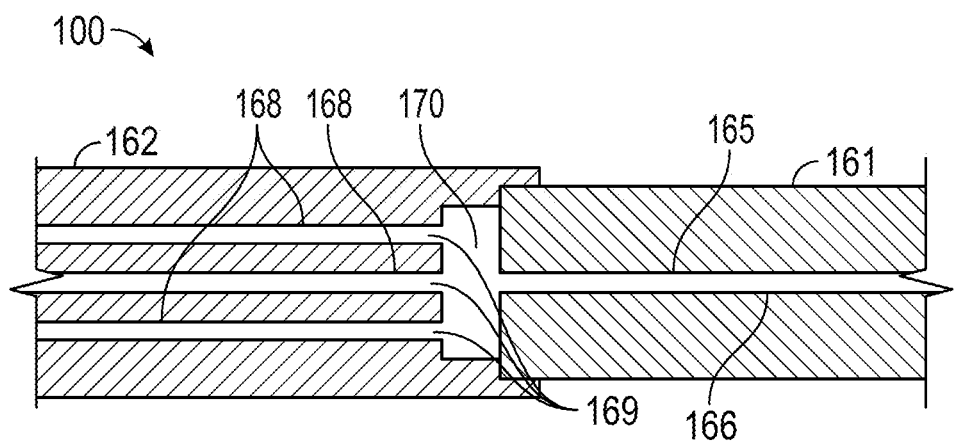

According to some embodiments, for example as shown in FIGS. 8A-8B, manufacture of an intraocular drainage device 100, which may be a very small manifold structure, can be accomplished using a two piece construction. As shown in FIGS. 8A and 8B, drainage device 100 can include a distal section 161 and a proximal section 162. The distal section 161 can, for example, correspond to the tube 106, and the proximal section 162 can, for example, correspond to the body 102. The proximal end of the distal section 161 can be joined together with the distal end of the proximal section 162. The distal section 161 can include an inlet lumen 165 which is fluidly coupled to an internal port 166 exposed at the proximal end of the distal section. The proximal section 162 can include a plurality of outlet lumens 168 which are fluidly coupled to a plurality of internal ports 169 exposed at the distal end of the proximal section 162. As shown in FIGS. 8A and 8B, for example, the plurality of internal ports 169 can be recessed relative to the distal end of the proximal section 162 to permit the formation of a distribution chamber 170 between the inlet lumen 165 and the plurality of outlet lumens 168 when the distal section 161 and the proximal section 162 are joined together. In other implementations, the internal port 166 may be recessed relative to the proximal end of the distal section 161, or both the internal port 166 and the plurality of internal ports 169 may be recessed relative to their respective ends to effect the formation of a distribution chamber 170 when joined together.

According to some embodiments, for example as shown in FIGS. 9A-9C, a drainage device 100 or component of a drainage device 100 such as body 102 can be manufactured using a soluble core 172 (e.g., a core made of a water soluble material) to form a multiple lumen or manifold structure. For example, as shown in FIG. 9A, a soluble core 172 can be formed into a pattern having a first extending member 173, which can correspond to a desired inlet lumen in the final configuration, and a plurality of second extending members 174 branching off of the first extending member, which can correspond to a desired plurality of branching outlet lumens in the final configuration. The second extending members may, for example be oriented at an angle of between 45 and 90 degrees relative to the first extending member (45 degrees is shown in FIG. 9A), or any other desired manifold geometry. As shown in FIG. 9B, for example, a part 131 that can correspond to body 102 or the entire drainage device 100 can be molded over the soluble core 172. The molded part 131 may be any appropriate material that is not soluble to the same solvent that will be used for dissolving the core 172. For example, the core 172 may be a water soluble material while the molded part 131 may be made of a water insoluble material. As shown in FIG. 9C, for example, the soluble core 172 may be dissolved with a solvent (e.g., water) to leave behind and replace the core with a manifold structure containing inlet lumen 165 and a plurality of outlet lumens 168 corresponding to the pattern of the initial core 172.

According to some embodiments, for example as shown in FIG. 10A, a multiple lumen structure may be formed by bonding together a plurality of small tubes 175 side by side. The side by side geometry may also, for example, facilitate formation of a plate-like geometry for the body 102 of the drainage device 100, where the tubes 175 can be arranged side by side along a major axis of the plate-like body.

According to some embodiments, for example as shown in FIG. 10B, the drainage device 100 such as body region 102 can include a plurality of polygons 132. The polygons 132 can, for example, be arranged in a series with regular spacing to form a plurality of outlet lumens 168 (e.g., fluid pathways) in intervening spaces between the polygons 132. In this example, the fluid pathways need not be in the form of lumens or tubular pathways extending through the structure.

Although various examples of construction of the drainage device 100 are described, it is contemplated that the drainage device 100 can be manufactured using other methods.

Figure 11:
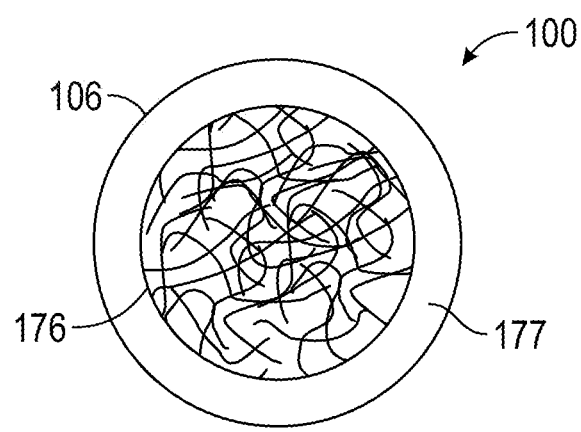
FIG. 11 is a cross section view of an intraocular drainage device, in accordance with some embodiments of the present disclosure.

According to some embodiments, for example as shown in FIG. 11, a drainage device 100 may include a tube 106 having a lumen 176 to provide a path for conveying fluid. The lumen 176 may include a sponge matrix disposed therein to facilitate flow restriction. The tube 106 with sponge matrix may be used instead of or in addition to a multiple lumen structure like that described herein.

Figure 12:
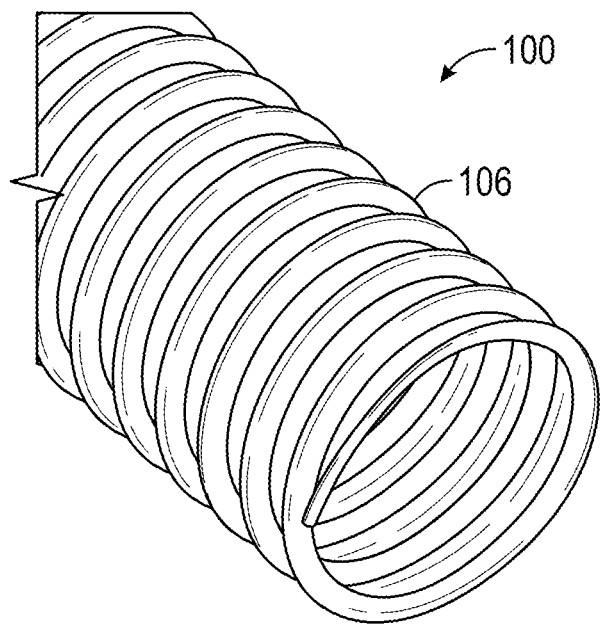
FIG. 12 is a three-dimensional view of an intraocular drainage device, in accordance with some embodiments of the present disclosure.

According to some embodiments, for example as shown in FIG. 12, a drainage device 100 may include tube 106 having an end with a coil that can provide circumferential corrugation to provide retention features. Additionally or alternatively, the coil may be configured with a shape memory material having predetermined curvature configured to conform with a curvature of a sclera so that the tube 106 may stay straight when housed within an inserter device 250 (e.g., within needle 253) but curl to conform with the curvature when ejected from the inserter device 250 (e.g., ejected from needle 253).

According to some embodiments, for example as shown in FIG. 13, the tube 106 may have a round cross sectional shape. Additionally or alternatively, the tube 106 may have any of a variety of other cross sectional shapes, such as D-shaped, oval, and the like.

According to some embodiments, for example as shown in FIG. 13, tube 106 may include multiple sets of retention features such as a first retention member 180 and second retention member 181, which can be disposed proximal to the first retention member 180. As shown in FIG. 13, for example, the first retention member 180 can include one or more fins that protrude radially outward from an exterior surface of the tube 106. The fin(s) can include a stop surface 183 on a proximal side thereof, which can be configured to abut patient tissue and/or device components to impede proximal, rearward movement of the tube 106 during an implantation procedure and/or after implantation. Additionally or alternatively, a distal side of the fins can include a ramped surface 184, which can slide against and/or expand an opening in patient tissue during implantation to facilitate deployment of the tube 106, or the distal end of the tube 106, through patient tissue. As shown in FIG. 13, for example, the ramped surface 184 can form an obtuse angle relative to an exterior surface of the tube 106. Additionally or alternatively, the stop surface 183 can have an angle of 90 degrees or less (e.g., to form a perpendicular or acute angle with respect to the outer surface of the tube 106). FIG. 13 shows an example in which the first retention member 180 includes a pair of discrete fins disposed on opposing sides of the tube 106. However, other implementations are contemplated in which any suitable number of one or more fins are included (e.g., one fin, two fins, three fins, five fins, ten fins, etc.), or in which the fins may be made continuous to extend circumferentially around the tube. Although examples are illustrated in which the stop surface 183 and the ramped surface 184 are substantially flat, other implementations are contemplated in which any one or more of these surfaces can be curved and/or have other geometries. Furthermore, although particular angles and ranges are described, other implementations are contemplated in which these surfaces may form angles outside of these particular angles or ranges.

According to some embodiments, for example as shown in FIG. 13, a second retention member 181 disposed proximal to the first retention member 180 can include friction enhancing features such as circumferentially extending bumps.

FIG. 14 is a cross section view of an eye 101 in which drainage device 100 according to the implementation shown in FIG. 13 is shown in situ when implanted into a patient's eye 101. As shown in FIG. 14, for example, a distal end of a tube of a drainage device 100 is disposed in an anterior chamber 115 of a patient's eye 101. The tube of drainage device 100 can be disposed through a scleral tract 186 such that the first retention member 180 (e.g., fins) can be disposed within the anterior chamber 115. The proximal side such as stop surface 183 of the first retention member can be seated against and abut patient tissue, such as a trabecular meshwork 187, to impede proximal movement or migration of the tube so that the tube 106 maintains a fluidic coupling to the anterior chamber 115. The distal side such as ramped surface 184 of the first retention member 180 may permit the tube to slide through an opening in the patient tissue.

As shown in FIG. 14, for example, the second retention member 181 can be disposed outside of the anterior chamber 115 and be retained against scleral tissue of sclera 113. The second retention member 181 may, for example, facilitate retention by enhancing friction between the second retention member 181 and the scleral surface. As shown in FIG. 14, the second retention member can be retained in the scleral tract 186 when the drainage device 100 is implanted. Additionally or alternatively, the second retention member can be retained against other tissue, such as scleral tissue in the conjunctival pocket between the conjunctiva 114 and the sclera 113.

According to some embodiments, for example as shown in FIG. 15, the first retention member 180 such as retention fins can additionally or alternatively facilitate retention of the tube 106 during deployment of the drainage device 100 during an implantation procedure. For example, the stop surface(s) 183 can abut a distal side of a needle 253 of an inserter device 250 so that the drainage device can remain housed within the needle during distal motion of the needle 253. The distal motion of the needle can also be used to form the scleral tract 186 as the needle 253 is advanced through the sclera 113 and into the anterior chamber 115. The drainage device 100 can be ejected from the inserter device 250 by, for example, retracting the needle 253 while a proximal surface of the first retention member 180 abuts the patient tissue to hold the tube 106 in place. During the implantation procedure, the fins can be disposed in respective slots 201 contained at the distal tip of the needle 253. The slots 201 may allow for the first retention member 180 to abut the distal side of the needle 253 without having the tube 106 protrude out of the distal end of the needle 253. However, other implementations are contemplated in which the slots 201 are omitted.

According to some embodiments, for example as shown in FIG. 16, a tube 106 may provide a drainage device without a need for a multiple lumen body. In such an embodiment, the tube 106 may, for example, provide a shunt with a single lumen terminating at a proximal end that drains into a conjunctival pocket. According to some embodiments, for example as shown in FIG. 16, the proximal end can include a plate 189 that can help separate the conjunctiva from the sclera. Additionally or alternatively, the plate 189 may help maintain a bleb. The plate 189 can, for example, be implemented with a ring of silicone as shown in FIG. 16. The plate 189 may, for example, be disposed on one side of the tube and be a substantially solid or monolithic structure with no internal lumens for fluid flow contained therein. Alternatively, other implementations are contemplated in which plate 189 is omitted.

Figure 17:
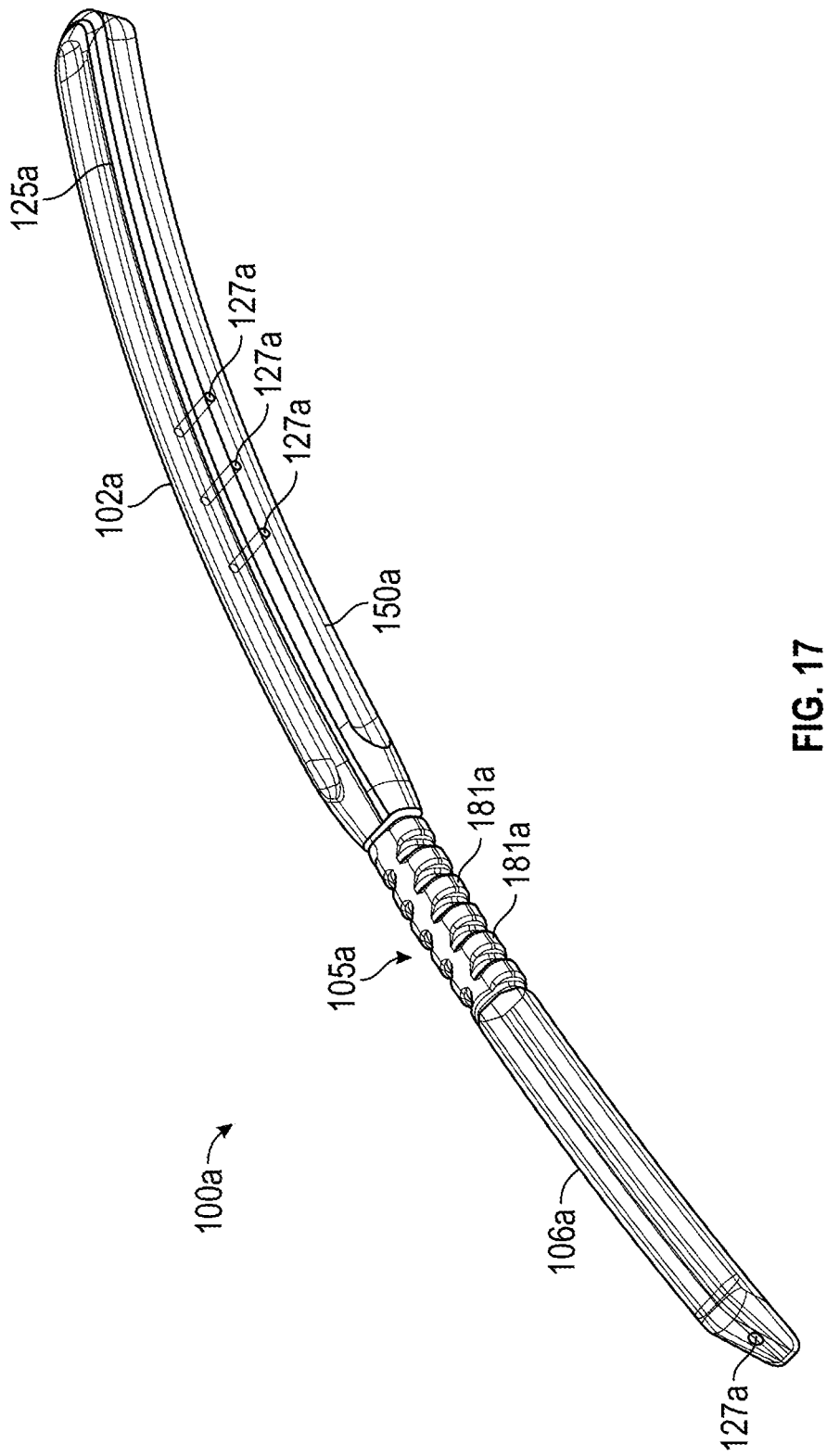
FIG. 17 is a three-dimensional view of an intraocular drainage device in a curved profile, in accordance with some embodiments of the present disclosure.

According to some embodiments, a drainage device 100a is provided. For example as shown in FIG. 17, the drainage device 100a may have a curved profile that includes a body 102a and a tube 106a. The curvature may be configured to match the contour of the eye, such as a 2.54 mm diameter curvature, for example. A patterned area 105a of the tube 106a may include multiple retention members 181a. For example, the patterned area 105a may be a large perpendicular pattern configured to provide for retention of the drainage device 100a in the sclera 113 of the eye 101, so as to prevent or impede forward or backward movement of the drainage device 100a after insertion in the eye 101. Multiple outlet ports 127a are disposed on the combined body 102a and tube 106a. For example, as shown in FIG. 17, one outlet port 127a may be disposed in the front end of the tube 106a, and three outlet ports 127a may be disposed on each side of the body 102a. An inlet port 125a is disposed down the interior of the body 102a. As discussed above, the outlet ports 127a in the body 102a may be disposed perpendicularly to the inlet port 125a, as shown in FIG. 17, or at an angle (e.g., 45 degrees), while the outlet port 127a at the front end of the tube 106a may be in line with the inlet port 125a. The body 102a may include one or more slots 150a (e.g., moats) configured to provide protection to the outlet ports 127a disposed in the body 102a. For example, some of the outlet ports 127a may be disposed within the slot 150a so that as tissue grows in to potentially occlude individual outlet ports 127a, the slot 150a provides for drainage along the slot or moat 150a.

Figure 18:
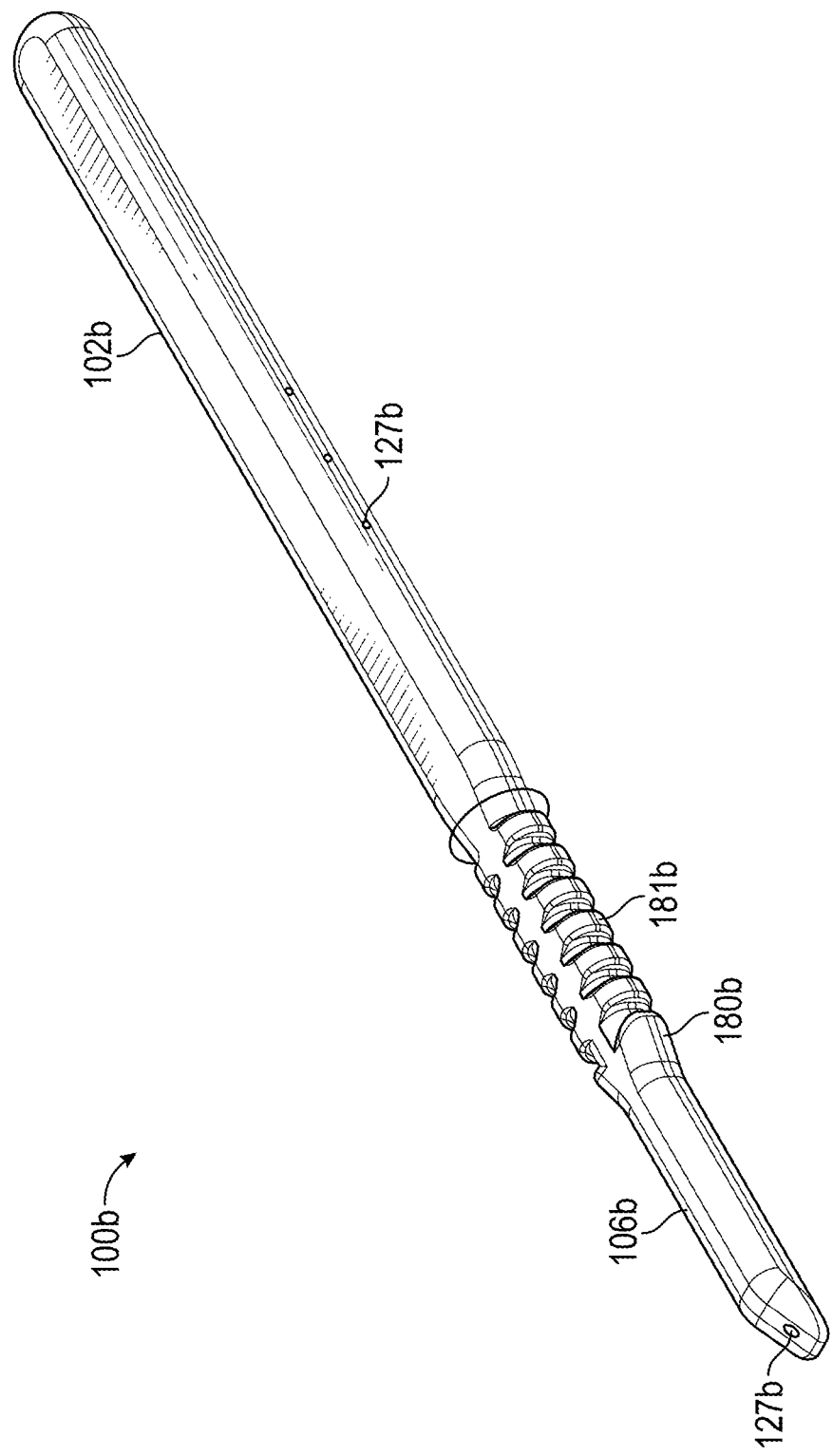
FIG. 18 is a three-dimensional view of an intraocular drainage device in a straight profile, in accordance with some embodiments of the present disclosure.
Figure 19:
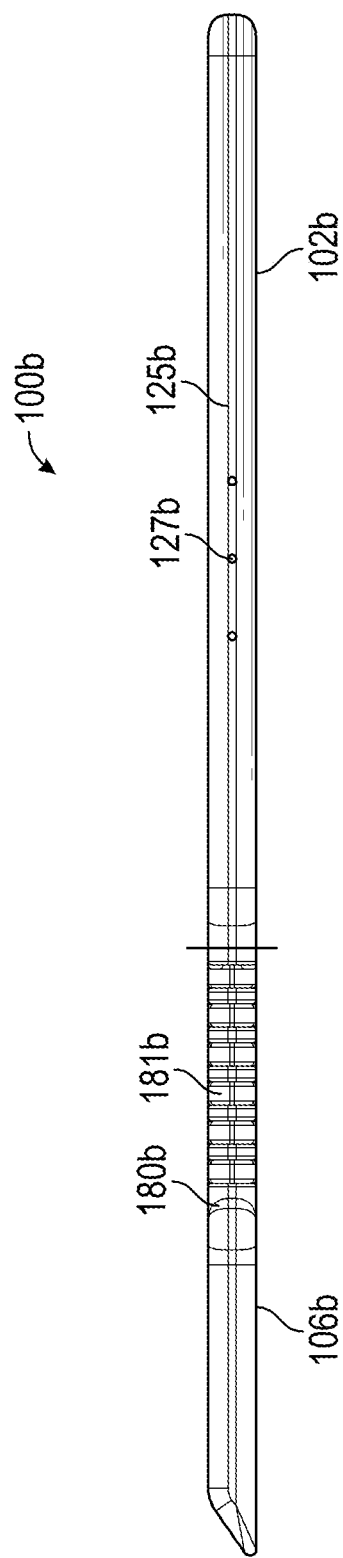
FIG. 19 is a side view of the intraocular drainage device of FIG. 18.
Figure 20:
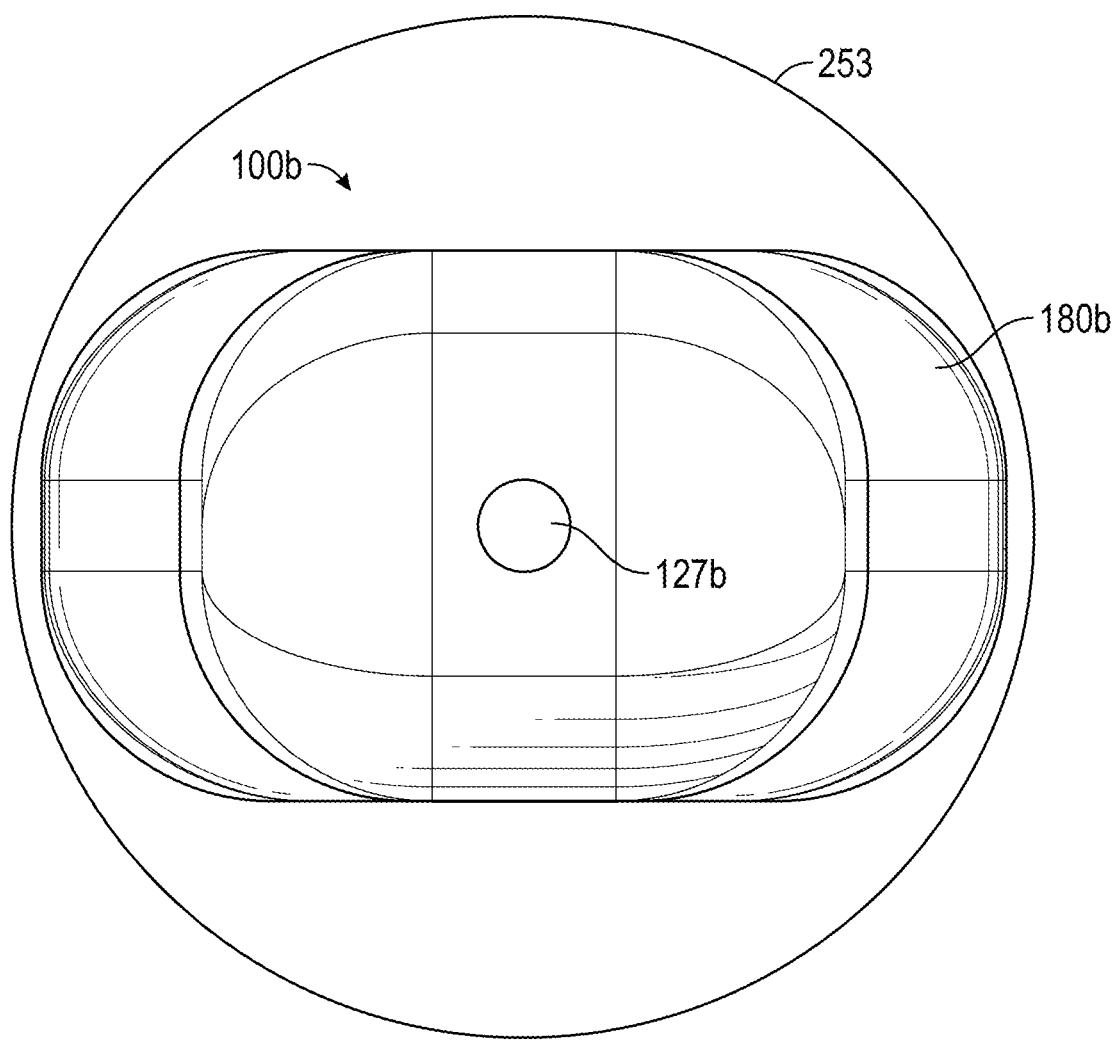
FIG. 20 is a front view of the intraocular drainage device of FIG. 18 disposed within a needle of an inserter device.

According to some embodiments, a drainage device 100b is provided. For example as shown in FIGS. 18-20, the drainage device 100b includes a body 102b and a tube 106b. A patterned area 105b of the tube 106b may include multiple retention members 180b and 181b. For example, retention members 180b may be radial fins protruding outward at an angle and retention members 181b may be ribs that extend outward perpendicularly. The number and size of ribs 181b may be provided for particular characteristics. For example, a decreased number of larger sized ribs 181b may provide for ease or efficiency in manufacturing, as well as increased integrity of the patterned area 105b (e.g., retention features). The retention members 180b and 181b may be configured to extend outward to match to the outer profile (e.g., width, diameter) of the body 102b. The patterned area 105b may be configured to provide for retention of the drainage device 100b in the sclera 113 of the eye 101, so as to prevent or impede forward or backward movement of the drainage device 100b after insertion in the eye 101. For example, the retention members 180b may be configured to sit in track or just inside the anterior chamber 115 of the eye 101. The retention members 181b may be compressible along the longitudinal axis of the drainage device 100b. For example, the retention members 181b may be compressed while disposed in the needle 253, thus shortening the length of the drainage device 100b, and may expand or spring back to an uncompressed state after insertion and retraction of the needle 253.

Figure 18A:
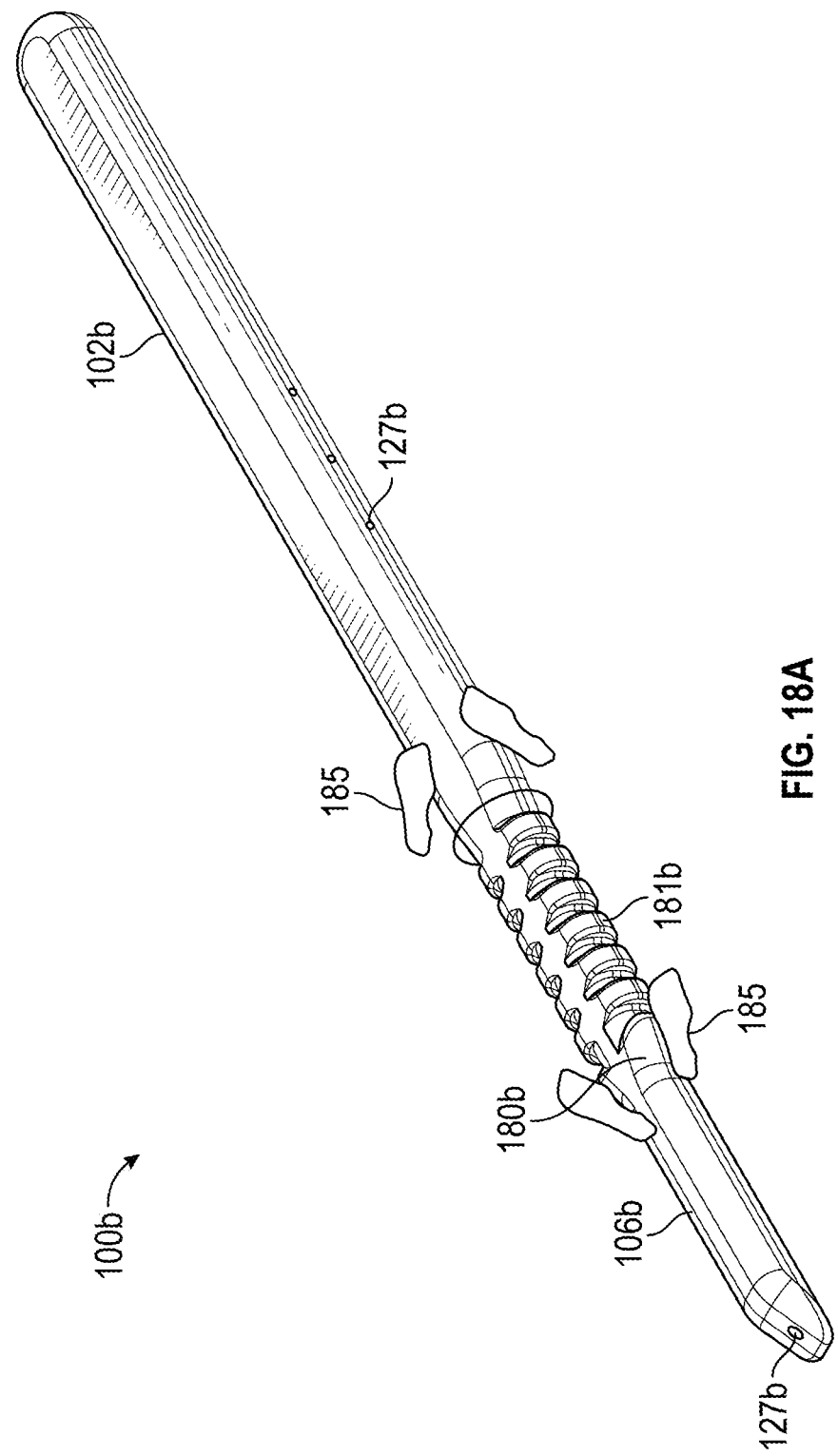
FIG. 18A is a three-dimensional view of the intraocular drainage device of FIG. 18 with additional retention members.

As shown in FIG. 18A, moveable retention members 185 may be disposed on the body 102b and/or the tube 106b adjacent to start and/or end of the retention members 181b.

Moveable retention members 185 may be flexible arms that are integral with the corresponding body 102b or tube 106b, or separate components that are coupled to the corresponding body 102b or tube 106b. The moveable retention members 185 may be squeezed inward (e.g., hugging the body 102b or tube 106b) while the drainage device 100b is disposed within an insertion device, while the moveable retention members 185 may spring open after insertion into the eye 101 (e.g., spring open on either side of the scleral thickness across the paracentesis) in order to provide further retention of the drainage device 100b in the sclera 113.

As shown in FIG. 18, one outlet port 127b may be disposed in the front end of the tube 106b, and three outlet ports 127b may be disposed on each side of the body 102b. An inlet port 125b is disposed down the interior of the body 102b. As discussed above, the outlet ports 127b in the body 102b may be disposed perpendicularly to the inlet port 125b, as shown in FIG. 18, or at an angle (e.g., 45 degrees), while the outlet port 127b at the front end of the tube 106b may be in line with the inlet port 125b.

As shown in FIG. 20, the drainage device 100b is configured to fit within a needle 253 of an inserter device 250. As the retention members 180b and 181b are sized and shaped not to exceed the outer profile of the body 102b, the size of the needle 253 may be selected based on the profile of the body 102b. The drainage device 100b may be configured in the straight profile shown in FIGS. 18 and 19, or in the curved profile as shown in FIG. 17.

Figure 21:
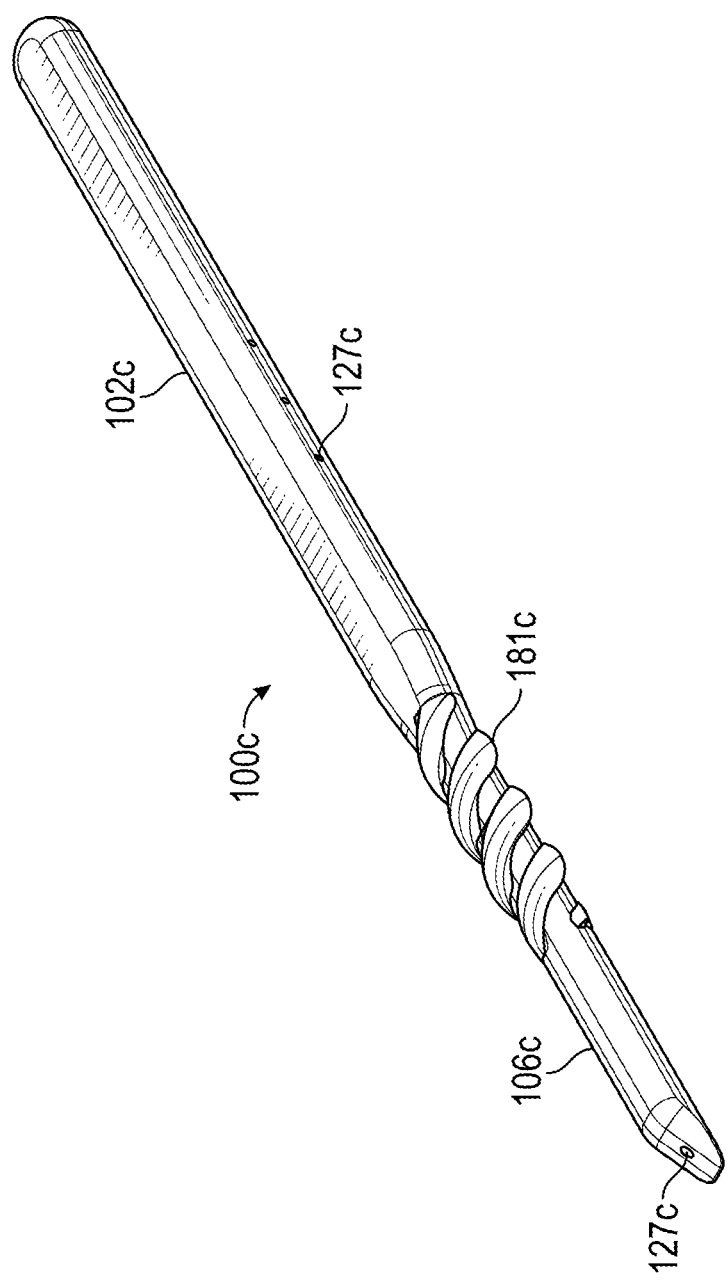
FIG. 21 is a three-dimensional view of an intraocular drainage device, in accordance with some embodiments of the present disclosure.
Figure 22:
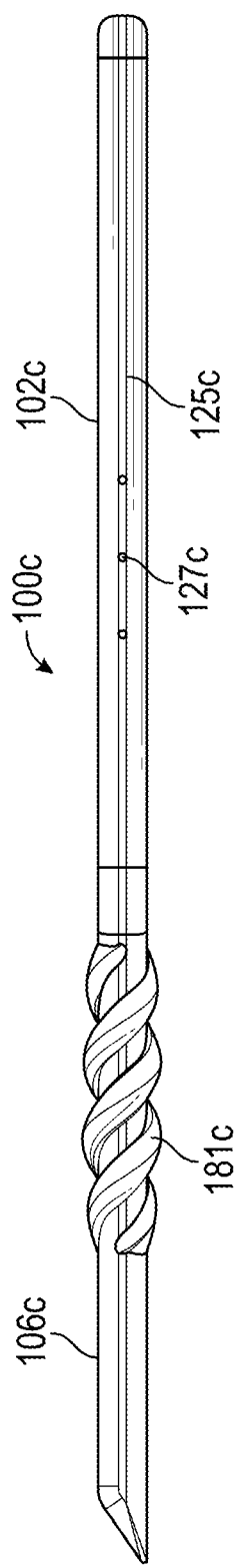
FIG. 22 is a side view of the intraocular drainage device of FIG. 21.
Figure 23:
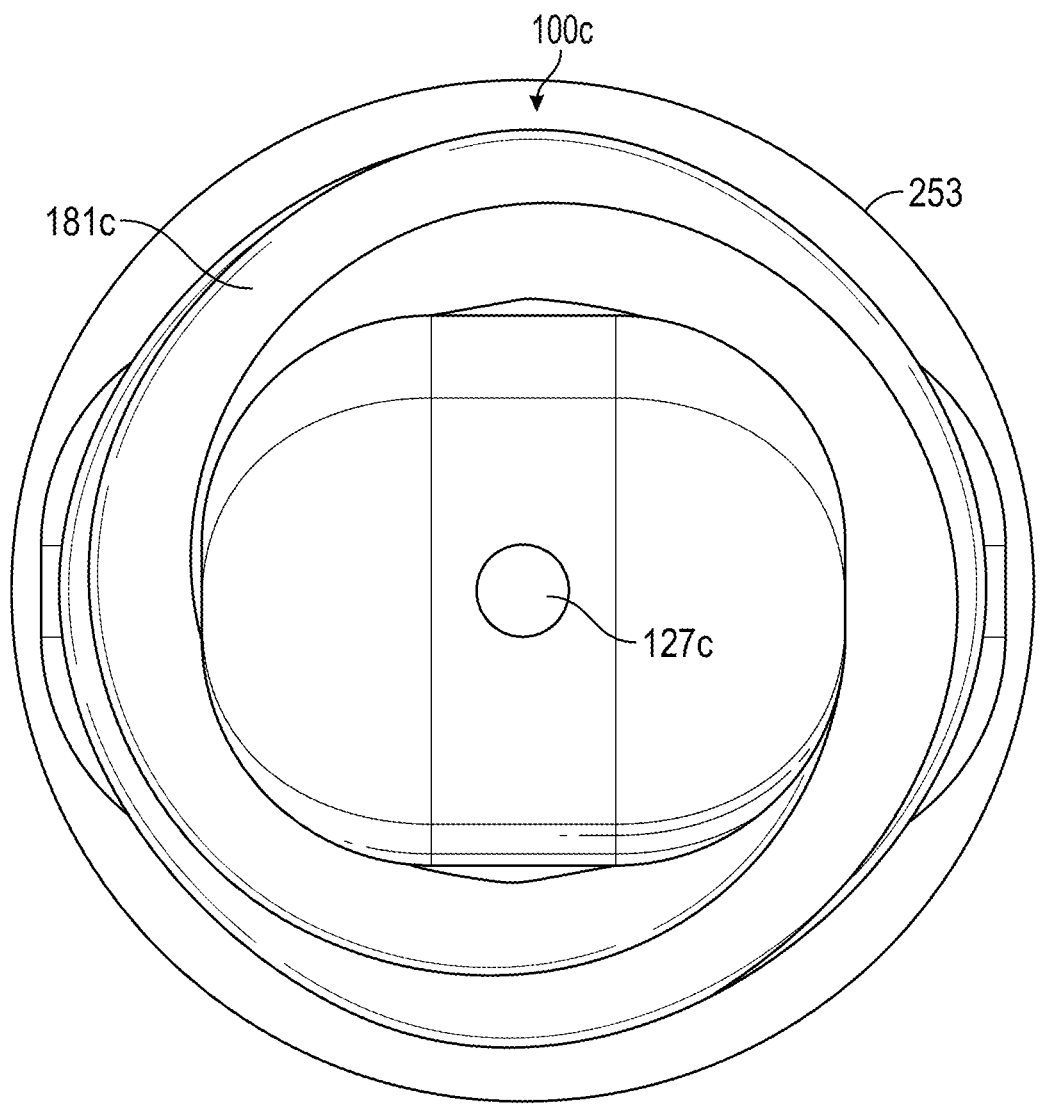
FIG. 23 is a front view of the intraocular drainage device of FIG. 21 disposed within a needle of an inserter device.

According to some embodiments, a drainage device 100c is provided. For example as shown in FIGS. 21-23, the drainage device 100c includes a body 102c and a tube 106c. A patterned area 105c of the tube 106c may include multiple retention members 181c. For example, retention members 181c may be twisted threads that extend outward to exceed the outer profile (e.g., width, diameter) of the body 102b. The patterned area 105c may be configured to provide for retention of the drainage device 100b in the sclera 113 of the eye 101, so as to prevent or impede forward or backward movement of the drainage device 100b after insertion in the eye 101. For example, the retention members 181c may be configured to stretch the tissue of the eye 101 and thus efficiently lodge and seal the drainage device 100c within the scleral track.

As shown in FIG. 21, one outlet port 127c may be disposed in the front end of the tube 106c, and three outlet ports 127c may be disposed on each side of the body 102c. An inlet port 125c is disposed down the interior of the body 102c, as shown in FIG. 22. As discussed above, the outlet ports 127c in the body 102c may be disposed perpendicularly to the inlet port 125c or at an angle (e.g., 45 degrees), while the outlet port 127c at the front end of the tube 106c may be in line with the inlet port 125c.

As shown in FIG. 22, the drainage device 100c is configured to fit within a needle 253 of an inserter device 250. As the retention members 181c are sized and shaped to exceed the outer profile of the body 102c, the size of the needle 253 may be selected based on the profile of the retention members 181c. The drainage device 100c may be configured in the straight profile shown in FIGS. 21 and 22, or in the curved profile as shown in FIG. 17.

Any of drainage devices 100, 100a, 100b, 100c may include orientation features disposed on or integrally formed with the body 102, 102a, 102b, 102c or the tube 106, 106a, 106b, 106c. An orientation feature can be a visual indicator (e.g., color, texture, pattern) that provides an indication of one end or the other (e.g., top or bottom, proximal or distal) of the drainage device 100, 100a, 100b, 100c, thereby providing a visual indication of the orientation of the drainage device 100, 100a, 100b, 100c after insertion into the eye 101.

Implantation Procedure

As described above, various implementations are contemplated in which intraocular drainage device 100 can be implanted in various locations of the eye ab-externally or ab-internally using an introducer instrument such as inserter device 250.

According to some embodiments, for example as shown in FIGS. 24A-24E and FIGS. 25A-25E, an implantation method can involve an ab externo approach in which the needle 253 of an inserter device 250 is inserted through a conjunctival incision 202 and through a sclera 113 to form a needle tract 186 in the sclera 113 (needle tract 186 is also sometimes referred to herein as a "scleral tract"). After the needle 253 forms the scleral tract 186, a distal tip of the needle 253 can enter the anterior chamber 115 to form a paracentesis for drainage of aqueous humour from the anterior chamber 115. The outflow pathway may extend through the same scleral tract 186 formed by the needle 253 during its approach to the anterior chamber 115. Although only one needle 253 is illustrated, implementations are contemplated in which one or multiple needles or sleeves can be included in the inserter device 250, which may be independently operable by one or more actuators.

The drainage device 100 can be initially held within the needle 253 and released by retraction of the needle 253 so that, after implantation, a distal end of the drainage device 100 remains in the anterior chamber 115 on the same side of the eye 101 entered by the needle 253. After implantation, a proximal end of the drainage device 100 can remain in the sub-Tenon's space between the conjunctiva 114 and the sclera 113 and more specifically between the Tenon's capsule 199 and sclera 113. An intermediate portion of the drainage device 100 between the distal end and proximal end can remain in the scleral tract 186 to convey the aqueous humour from an inlet port at the distal end of the drainage device 100 to one or more outlet ports at the proximal end of the drainage device 100. According to some embodiments, to facilitate the ab externo implantation method, the drainage device 100 can be initially held within the needle 253 with an orientation in which the distal end of the drainage device 100 containing the inlet port faces a release port of the needle 253 at a distal tip of the needle, while a proximal end of the drainage device 100 faces away from the release port of the needle 253 and faces towards a handle 254 of the inserter device 250. In some embodiments, the inserter device 250 is configured to deliver a fluid (such as an ophthalmic viscoelastic), or a gas (such as air, SF6 or C3F6) to separate tissue planes (such as the Tenon's capsule and the sclera) prior to implantation of the injected drainage device 100 between the separated tissue planes.

FIGS. 24A-24E show an example of an implantation procedure that involves a conjunctival incision 202 made closer to a limbus 198 than a sub-Tenon's space or other retaining space within which portions of the drainage device 100 will be held. As shown for example in FIGS. 24A-24E, the implantation procedure can involve initially inserting the needle 253 through the incision 202, then manipulating a proximal portion of the device 100 such as body 102 into the sub-Tenon's space from a different angle through the same incision 202.

Figure 24A:
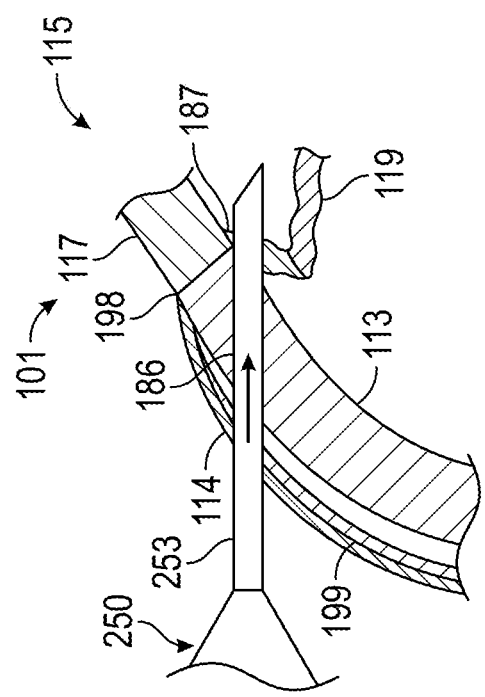
FIGS. 24A-24E are cross section views of an implantation procedure using an inserter device, in accordance with some embodiments of the present disclosure.

As shown in FIG. 24A, prior to insertion of the needle 253, an incision 202 can be formed in a conjunctiva 114. The incision 202 can be made, for example, approximately 3 millimeters (mm) away from the limbus 198 of the eye 101, although it is contemplated that other locations may be suitable for this incision. As shown in FIG. 24A, the incision 202 can be made using a blade 203 such as a scalpel or other appropriate surgical instrument which may be separate from the inserter device 250. However, other implementations are contemplated in which the inserter device 250 itself is used to make the initial incision 202. The incision 202 can be made through the conjunctiva 114 and through the Tenon's capsule 199 of the eye 101. Although Tenon's capsule 199 is shown as a separate layer in FIG. 24A, it is noted that the Tenon's capsule 199 can become integral with the conjunctiva 114 in a region close to the limbus 198. Through the incision 202, a pocket between the conjunctiva 114 and sclera 113 may be formed or opened up using the blade 203 or any other appropriate tool to dissect the Tenon's capsule 199 from the episclera (outermost layer of the sclera 113). As further described below, the pocket may provide a space for a portion of the drainage device 100 such as body 102 to be later inserted and retained.

Figure 24C:
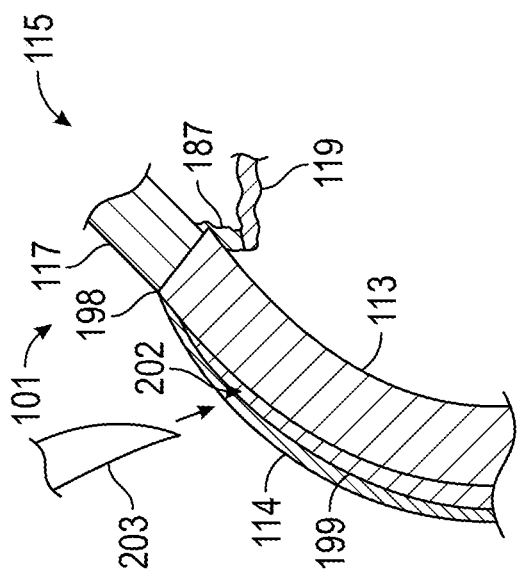
Figure 24B:
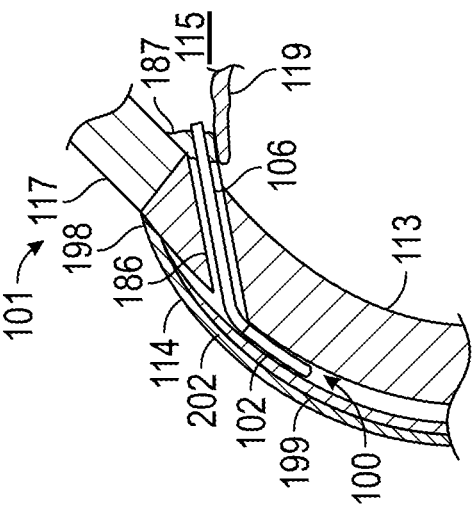

As shown in FIG. 24B, the needle 253 of inserter device 250 can be inserted through the incision 202. The needle 253 can be advanced distally through the sclera 113 to form a scleral tract 186, and advanced further so that a distal tip of the needle 253 enters the anterior chamber 115 through the trabecular meshwork 187 or other eye tissue enclosing the anterior chamber 115. The needle 253 can be advanced distally by, for example, the surgeon or user moving the handle to advance the entire inserter device 250 including the needle 253 distally and/or by manipulating an actuator to advance the needle 253 distally relative to the handle 254.

As shown in FIG. 24C, the needle 253 can be retracted to leave the intraocular drainage device 100 in place with a distal portion of the drainage device 100 such as a distal end of the tube 106 disposed within the anterior chamber 115. As shown in FIG. 24C, retraction of the needle 253 can also leave a portion of the drainage device 100, such as an intermediate or proximal portion of tube 106 in place in the scleral tract 186 that was earlier formed by the distal movement of the needle 253. The needle 253 can be retracted, for example, by manipulating the actuator 252 (not visible in FIGS. 24A-24E) to activate an internal mechanism within the handle and coupled to the needle 253. FIG. 24C shows the needle 253 partially retracted with a portion of the drainage device 100 exposed and a remaining portion of the drainage device 100 still held within the needle 253.

Figure 24D:
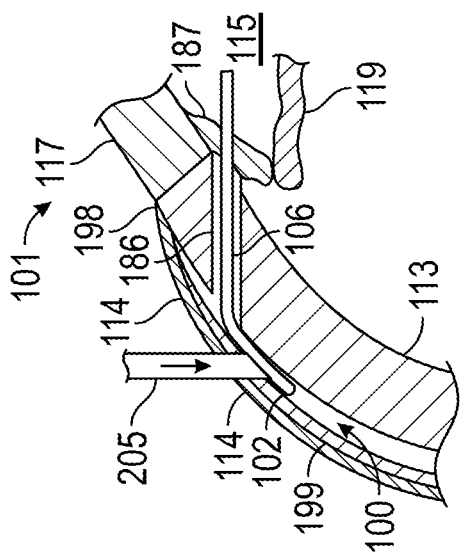

As shown in FIG. 24D, after needle 253 is retracted out of the sclera 113 and out of the scleral tract 186, a portion of the drainage device 100, such as all or a portion of body 102, can be inserted into the pocket between the conjunctiva 114 and the sclera 113. The drainage device 100 may be inserted into pocket by further manipulating the drainage device 100 using a tool 205, which can, for example, be the same inserter device 250 or a separate instrument. The drainage device 100 may be manipulated at this stage by pivoting or otherwise approaching the pocket at a different angle relative to the angle of approach used with the needle 253 during formation of the needle tract 186. According to some embodiments, retention features in the drainage device 100 such as the retention features described above may permit the drainage device 100 to remain in place without a need for suturing the drainage device 100 to the tissue of the eye 101.

According to some embodiments, the drainage device 100 can be flexible and housed within the needle in a compressed state. For example, the drainage device 100 may be squeezed, folded, or otherwise compressed against an interior surface of the needle 253 to permit the drainage device 100 to have a smaller form factor prior to release into the intraocular site of the patient's eye 101. Upon retraction of the needle 253 and release of the drainage device 100, compression applied to the compressed portions of the drainage device may be released so that the drainage device 100 is uncompressed and allowed to self-expand in the intraocular site (e.g., in the pocket) to an uncompressed state that is larger in one or more dimensions (e.g., larger in diameter or larger in a dimension along the major axis of the body 102) than a diameter of the needle 253. However, while examples are described in which flexible drainage device 100 is compressed, other implementations are contemplated in which the drainage device 100 is not compressed when held by the needle 253 and/or not expanded when released from the needle 253.

Figure 24E:
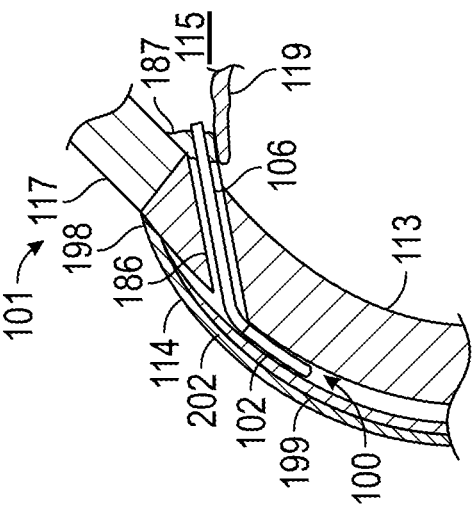

FIG. 24E shows the drainage device 100 after insertion into the pocket. As shown in FIG. 24E, the body 102 or portions of the body 102 may be held within the sub-Tenon's space while the tube 106 or portions of the tube 106 may be held within the anterior chamber 115. The drainage device 100 can be retained so that one or more inlet ports (not visible in FIG. 24E) of the drainage device 100 contact the anterior chamber 115 and one or more outlet ports (not visible in FIG. 24E) of the drainage device 100 contact the space between the conjunctiva 114 and the sclera 113.

FIGS. 25A-25E show an example of an implantation procedure that involves inserting the needle 253 through an incision 202 made farther away from a limbus 198 than the space between the conjunctiva and the sclera within which portions of the implanted drainage device will be held. As shown for example in FIGS. 25A-25E, the implantation procedure can involve initially inserting the needle 253 through the incision 202, then leaving a proximal portion of the drainage device 100 such as body 102 in the sub-Tenon's space by continuing to retract the needle, without a need to substantially pivot the inserter device 250 to leave the drainage device in the sub-Tenon's space.

As shown for example in FIG. 25A, a conjunctival incision 202 can be made, for example, farther than approximately 3 millimeters (mm) away from the limbus 198 of the eye 101, although it is contemplated that other locations may be suitable for this incision. As shown in FIG. 25A, the incision 202 can be a needle incision made by inserting the needle 253 of the inserter device 250 through the conjunctiva 114. The incision 202 can be made through the conjunctiva 114 and through the Tenon's capsule 199 of the eye 101. A pocket between the conjunctiva 114 and sclera 113 may be formed at this stage through the incision 202 in a space above the incision (closer to the limbus 198 than the incision 202), or the procedure may proceed without a need to open up a pocket at this stage.

As shown in FIG. 25B, the needle 253 can be advanced distally through the sclera 113 to form a scleral tract 186, and advanced further into the anterior chamber 115 through the trabecular meshwork 187 or other eye tissue enclosing the anterior chamber 115.

As shown in FIG. 25C, the needle 253 can be retracted to leave the intraocular drainage device 100 in place with a distal portion of the drainage device 100 such as a distal end of the tube 106 disposed within the anterior chamber 115. As shown in FIG. 25C, retraction of the needle 253 can also leave a portion of the drainage device 100, such as an intermediate or proximal portion of tube 106 in place in the scleral tract 186 that was earlier formed by the distal movement of the needle 253. FIG. 25C shows the needle 253 partially retracted with a portion of the drainage device 100 exposed and a remaining portion of the drainage device 100 still held within the needle 253.

As shown in FIG. 25D, after needle 253 is retracted out of the sclera 113 and out of the scleral tract 186, the needle can continue to be retracted so that a portion of the drainage device 100, such as all or a portion of body 102, can be left in place in a retaining space between the conjunctiva 114 and the sclera 113. In this manner, the initial incision can be considered to be underneath, or farther away from the limbus 198 than, the retaining space of the drainage device. This may, for example, avoid a need for separate pivoting or manipulation of the drainage device 100 from a different approach angle to fix the drainage device 100 into the retaining pocket. Additionally or alternatively, this may provide a less invasive procedure than implementations involve separate manipulation to fit the drainage device 100 into the pocket from above. Retention features in the drainage device 100 such as the retention features described above may permit the drainage device 100 to remain in place without a need for suturing the drainage device 100 to the tissue of the eye 101.

FIG. 25E shows the drainage device 100 retained in the space after retraction of the needle. As shown in FIG. 25E, the body 102 or portions of the body 102 may be held within the sub-Tenon's space while the tube 106 or portions of the tube 106 may be held within the anterior chamber 115. The drainage device 100 can be retained so that one or more inlet ports (not visible in FIG. 25E) of the drainage device 100 contact the anterior chamber 115 and one or more outlet ports (not visible in FIG. 25E) of the drainage device 100 contact the space between the conjunctiva 114 and the sclera 113.

Inserter Device

Figure 26:
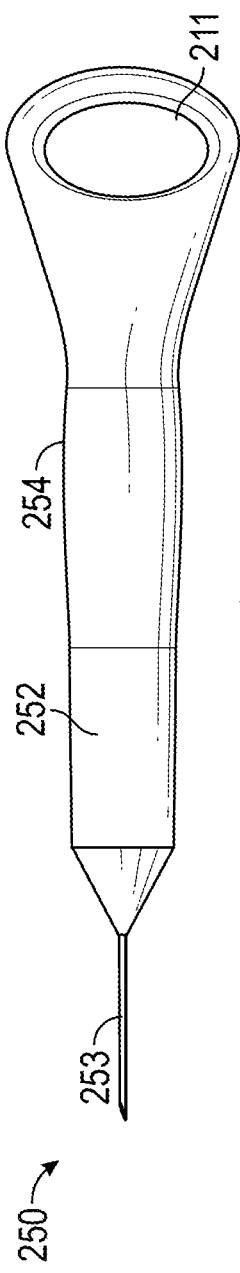
FIG. 26 is a top view of an inserter device, in accordance with some embodiments of the present disclosure.

According to some embodiments, for example as shown in FIG. 26, an actuator 252 of an inserter device 250 can include a trigger button disposed on a side of the handle 254, which can, for example, be operated using a thumb or index finger of a surgeon when holding the handle 254 using a pencil grip. Additionally or alternatively, the inserter device 250 can include a finger loop 211 disposed on a proximal end of the inserter device 250, opposite to the distal end of the inserter device 250 containing the needle 253 through which the drainage device 100 can be released. The finger loop 211 can, for example, provide an ergonomic feature that can be pulled by a user to create a vacuum in a vacuum chamber within the handle. The vacuum chamber can be configured to apply a vacuum force to retract the needle 253 upon depression of the actuator 252. It should be understood that the vacuums described herein need not be perfect vacuums, but can generally include any suitable voids with air removed to create a pressure differential that causes a vacuum force to be applied.

FIGS. 27A-27D are cut away views of an inserter device 250 according to the implementation shown in FIG. 19 at various example stages of operation. As shown for example in FIGS. 27A-27D, the inserter device 250 can include a handle 254 and a needle 253 disposed on a distal end of the handle 254. A front plunger 215 can be coupled to the needle 253 and disposed within the handle 254. The front plunger 215 can, for example, be fixedly attached directly or indirectly to the needle 253 so that the needle 253 moves with the front plunger 215. The front plunger 215 can be disposed distal to a front vacuum chamber 219 so that a vacuum created in the vacuum chamber 219 can apply a proximal force to the front plunger 215, which can in turn retract the needle 253 together with the front plunger 215.

FIGS. 27A-27D also show other components that can be included to facilitate creation of a vacuum within the inserter device 250 and retraction of the needle 253 based on the vacuum. For example, a rear plunger 213 can be disposed proximal to the front plunger 215 and reciprocably disposed within a channel 221 so that the rear plunger 213 can translate back and forth. The rear plunger 213 can, for example as shown in FIGS. 27A-27D, be made smaller than the front plunger 215. A charging section 233 can be disposed on a proximal end of the handle 254 and be retractable proximally relative to the handle 254. Retraction of the charging section 233 can be configured to expand a rear vacuum chamber 218 to create a vacuum therein. The vacuum in the rear vacuum chamber 218 can apply a proximal force on the rear plunger 213 to cause the rear plunger to move proximally within the channel 221, in turn creating a vacuum within the front vacuum chamber 219. A valve 229, such as, for example, a duckbill valve, can be coupled to the rear vacuum chamber 218 to permit release of pressure when the charging section 233 is moved distally to contract the rear vacuum chamber 218. A finger loop 211 can be disposed on or otherwise coupled to the charging section 233 to facilitate retraction of the charging section 233 by pulling on the finger loop. Each of the front vacuum chamber 219 and rear vacuum chamber 218 may be sealed chambers (e.g., sealed with an O-ring or other sealing member).

Figure 27A:
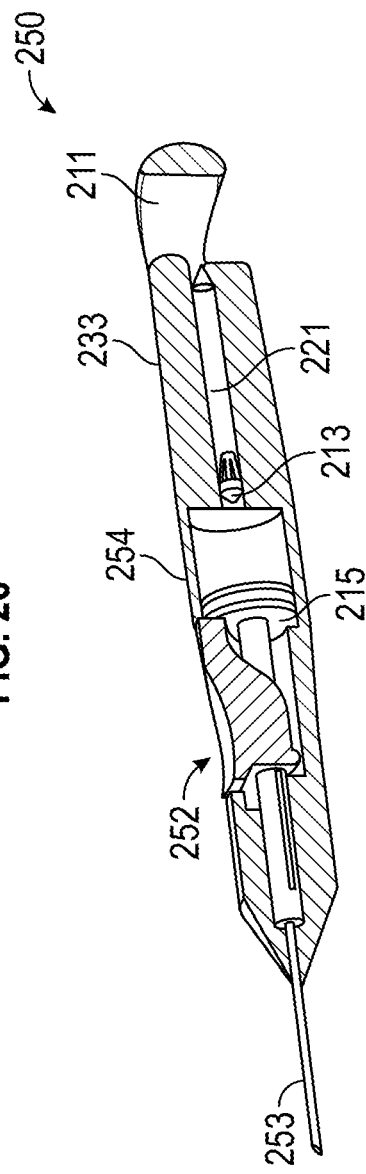
FIGS. 27A-27D are cutaway views of an inserter device at various phases of operation, in accordance with some embodiments of the present disclosure.

FIG. 27A shows the inserter device 250 during a packaged phase, which can correspond to be an initial phase as the device 250 is delivered to a user. At this stage, there may be no vacuum within the inserter device 250, and thus no vacuum within the front vacuum chamber 219. The needle 253 (e.g., a metal sleeve) and the front plunger 215 can be in a forward or distal position. An intraocular drainage device (not visible in FIG. 27A) can be held within the needle 253. The actuator 252 can be implemented as a trigger button that is held up in a locked position at this stage. The rear plunger 213 can be disposed in a forward, distal position at this stage.

Figure 27B:
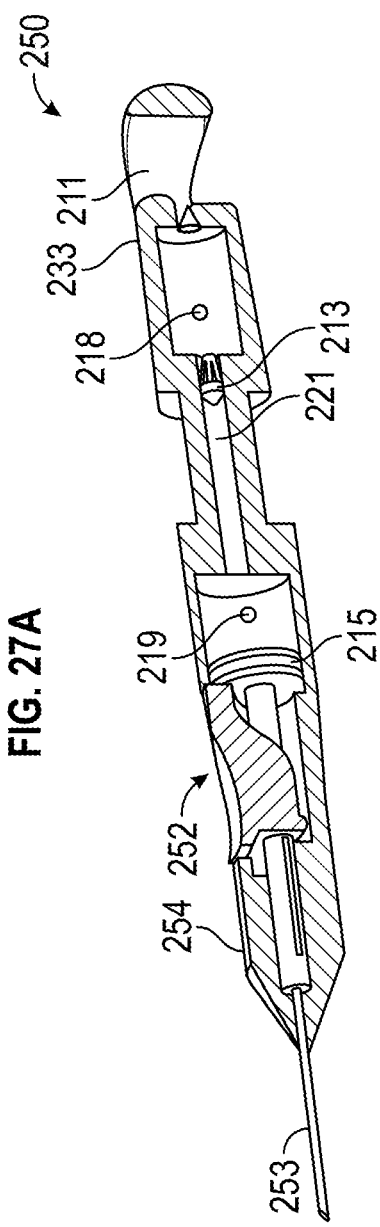

FIG. 27B shows the inserter device 250 during a charging phase, which can be used to create a vacuum within the device. During the charging phase, a user can retract the charging section 233 relative to the handle 254 (e.g., by pulling on the finger loop 211), which can expand the rear vacuum chamber 218 to create a vacuum in each of the front and rear vacuum chambers. In particular, the vacuum created in the rear vacuum chamber 218 may apply a proximal vacuum force to the rear plunger 213, which can cause the rear plunger 213 to translate proximally in the channel 221 and thus create a vacuum in the front vacuum chamber 219. Although the vacuum in the front vacuum chamber 219 can apply a proximal vacuum force to the front plunger 215, the front plunger 215 can remain in the distal position as it is held in place by the trigger button actuator 252 or mechanism coupled to the trigger button actuator.

Figure 27C:
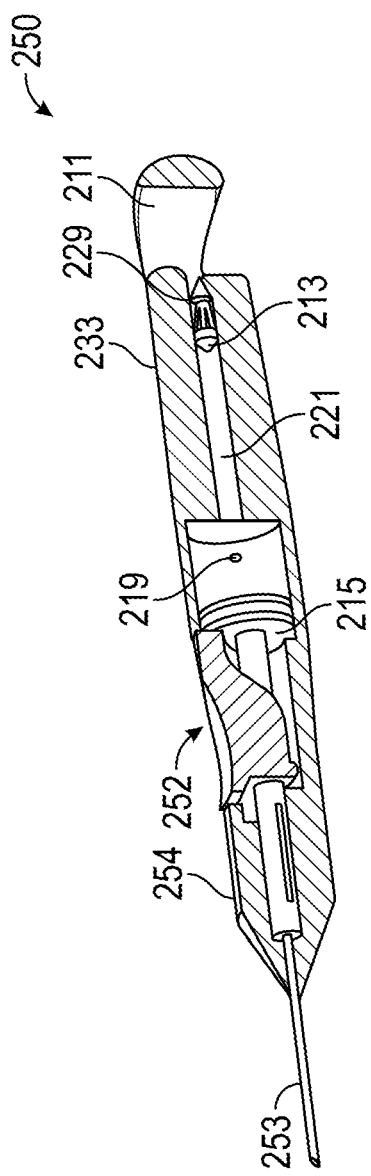

FIG. 27C shows the inserter device 250 during an activation phase. At this stage, the user can push the charging section 233 distally relative to the handle 254. This can cause positive pressure to be released through the valve 229. Additionally or alternatively, the distal movement of the charging section 233 can cause a safety catch coupled to the trigger button actuator 252 to be released to allow the trigger button to be depressed. The front plunger 215 and needle 253 can remain held in the forward distal position by the actuator 252 at this stage.

Figure 27D:
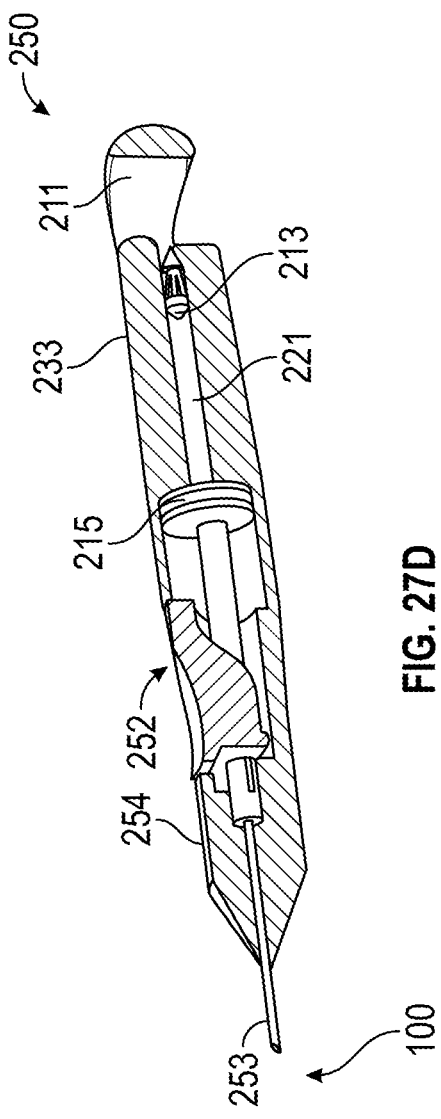

FIG. 27D shows the inserter device 250 during a retraction phase. During the retraction phase, the trigger button actuator 252 can be depressed by the user, releasing the front plunger 215 to permit the front plunger 215 to translate proximally relative to the handle 254, and retract together with the needle 253 to expose the intraocular drainage device 100. In particular, the vacuum within the vacuum chamber 219 can apply a proximal vacuum force to the front plunger 215. The proximal vacuum force can be counteracted by the trigger button when the trigger button is in the up position to hold the front plunger 215 and needle 253 in place. Pressing the trigger button can remove this counteracting force to permit the proximal movement of the plunger 215 and the needle 253 upon button press.

According to some embodiments, for example as shown in FIGS. 28A-28D, the inserter device 250 can include an actuator 252 implemented as a slidable and pressable button coupled to the needle 253. The needle 253 can be translatable upon sliding of the button relative to the handle 254, while pressing of the button can cause the intraocular drainage device 100 to be released from within the needle 253. In various implementations, the slidable and pressable button can be operable to translate the needle 253 distally (deployment), proximally (retraction), or both distally and proximally.

Figure 28A:
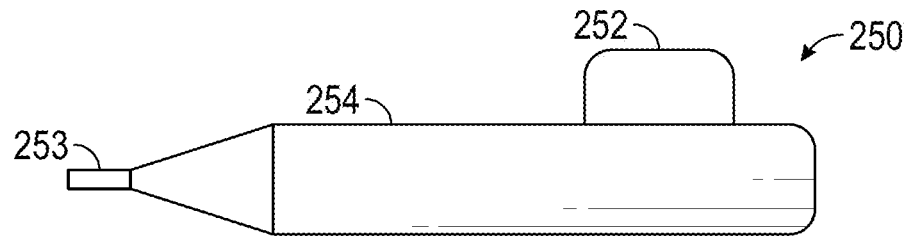
FIGS. 28A-28D are side views of an inserter device at various phases of operation, in accordance with some embodiments of the present disclosure.
Figure 28B:
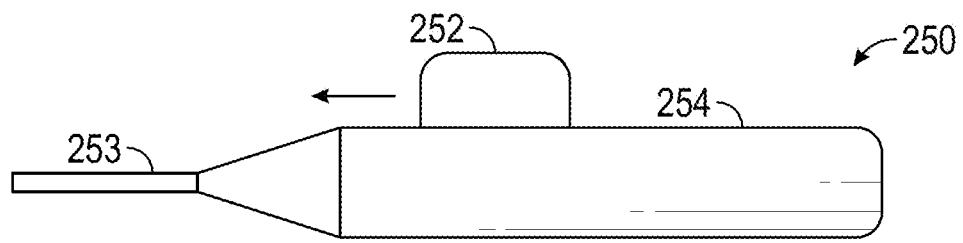
Figure 28C:
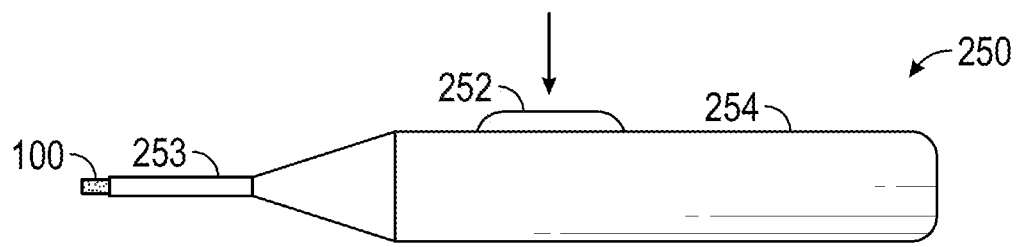
Figure 28D:
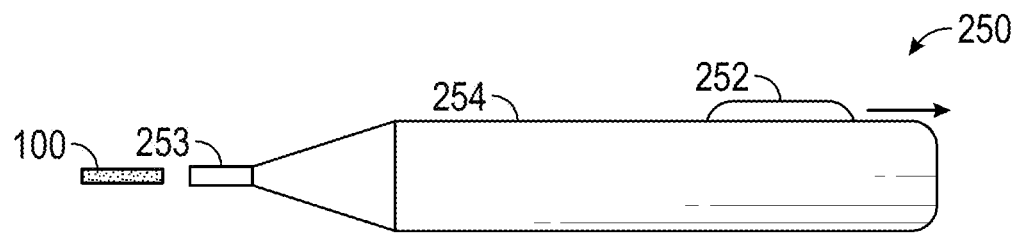

FIGS. 28A-28D show the inserter device 250 implemented with a slidable and pressable button at various stages of operation. FIG. 28A shows the inserter device 250 during an initial phase where the slidable and pressable button actuator 252 is in an upward and proximal position, and the needle 253 is also in a proximal position with an intraocular drainage device (not visible in FIG. 28A) held therein. FIG. 28B shows the inserter device 250 during a deployment phase. The actuator 252 remains in an upward position to hold the drainage device within the needle 253, and the actuator is translated distally by a user to deploy the needle 253 distally (e.g., to facilitate insertion of the needle 253 into an anterior chamber or other eye compartment). FIG. 28C shows the inserter device 250 during an engagement phase. At this stage, the button actuator 252 is pressed to cause the drainage device 100 to be released from the needle. By way of example, pressing the button can cause the engagement of tensioners and/or a tissue grip. FIG. 28D shows the inserter device 250 during a retraction phase. At this stage, the user can translate the slidable button actuator 252 proximally to retract the needle 253 from around the drainage device 100. The actuator 252 can be translated proximally while in a depressed position to facilitate release of the drainage device 100 in the implantation site.

Figure 29C:
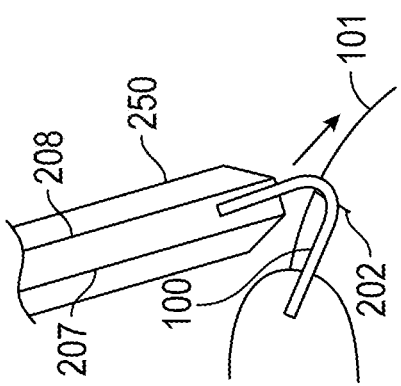
Figure 29A:
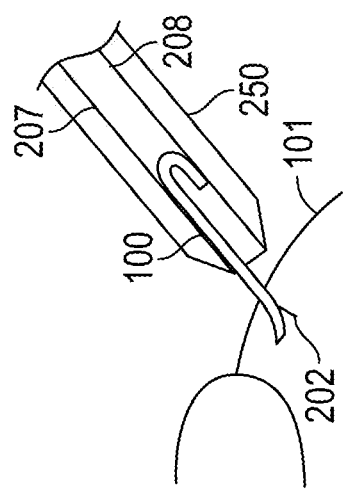
Figure 29A:
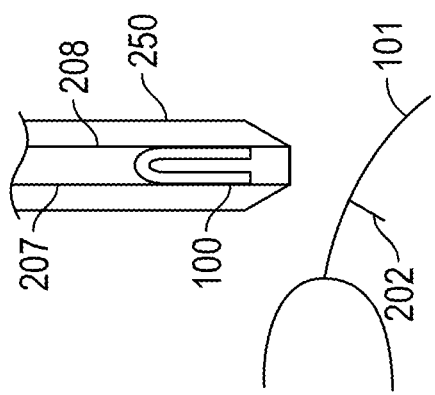

According to some embodiments, for example as shown in FIGS. 29A-29C, the inserter device 250 can include a two arm manipulator. The two arm manipulator can be operable by one or more actuators (not visible in FIGS. 29A-29C) to permit portions of the drainage device 100 to be inserted into different compartments of the eye through a single incision 202. For example, the two arm manipulator may facilitate an implantation procedure similar to that shown in FIGS. 24A-24D, where a first arm 207 facilitates insertion of a distal end of the drainage device 100 into an anterior chamber, while a second arm 208 facilitates insertion of a proximal end of the drainage device 100 into a space between a conjunctiva and a sclera, such as a sub-Tenon's space, from a different angle.

FIGS. 29A-29C shows the inserter device 250 implemented with two arm manipulator at various stages of operation. As shown for example in FIG. 29A, the two arm inserter device 250 can be inserted into a single incision 202 of an eye 101, such as an incision in a conjunctiva to facilitate an ab externo approach. As shown in FIG. 29B, a first arm 207 can engage a portion such as a distal portion of the drainage device 100 and manipulate the drainage device 100 through the incision to place the portion of the drainage device 100 into the anterior chamber. In some embodiments, an actuator (not visible in FIG. 29B) can be operated to manipulate the first arm 207 and place the portion of the drainage device 100 into the anterior chamber, and/or operated to release the portion of the drainage device 100 when it is in the desired location. As shown in FIG. 29C, a second arm 208 can be engaged with another portion such as a proximal portion of the drainage device 100. A user can pivot the inserter device 250 to approach the sub-Tenon's space or other space from a different angle through the same incision 202. In some embodiments, an actuator (not visible in FIG. 29C), which can be the same or separate from the actuator that manipulates the first arm 207, can be operated to manipulate the second arm 208 and place the other portion of the drainage device into the sub-Tenon's space, and/or operated to release the other portion of the drainage device 100 when it is in the desired location. The one or more actuators can be configured to operate the first arm and the second arm independently. The arrow in FIG. 29C shows a direction of advancement for the second arm 208, which can be substantially transverse or tangential to the scleral or conjunctival surface.

Figure 30A:
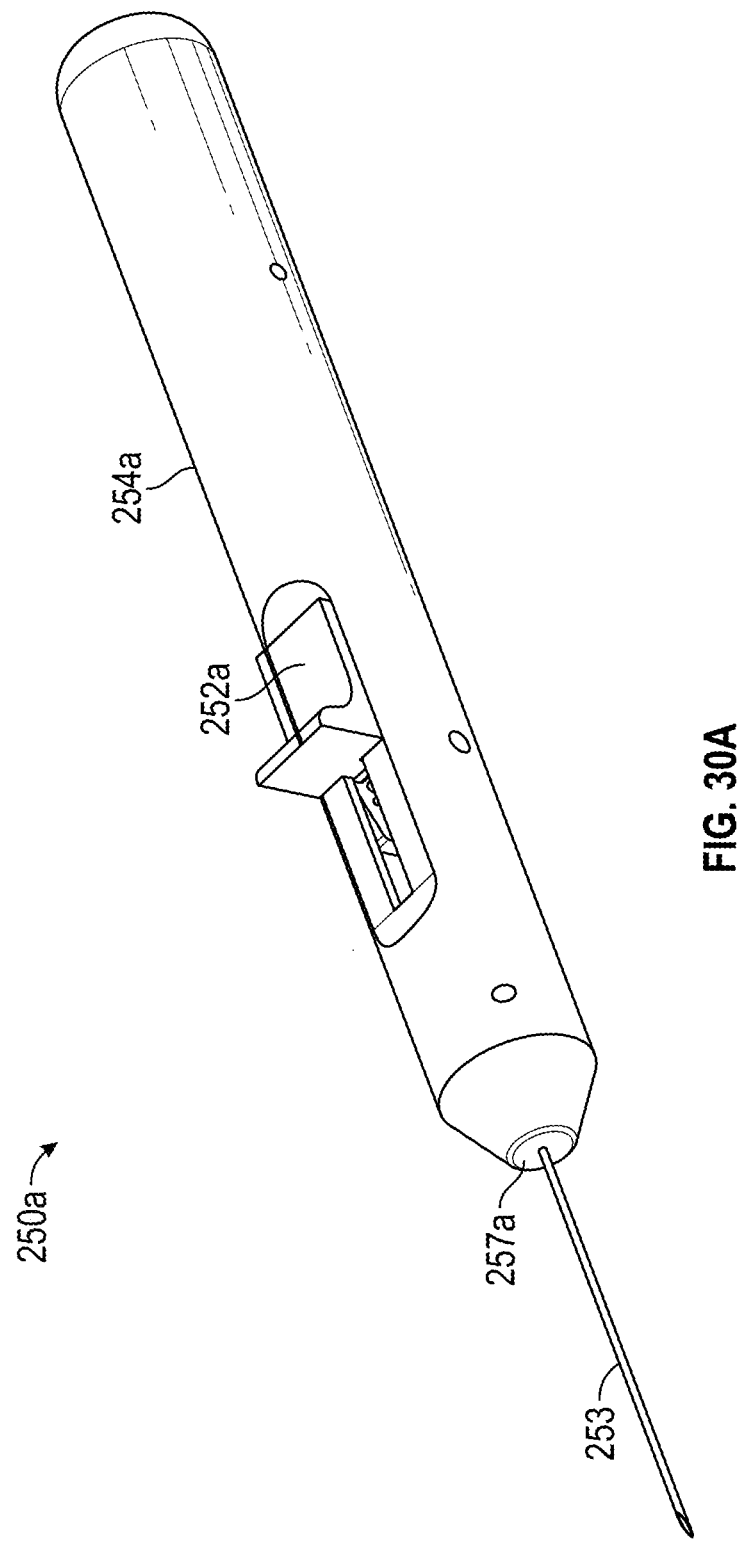
FIG. 30A is a three-dimensional view of an inserter device, in accordance with some embodiments of the present disclosure.
Figure 30B:
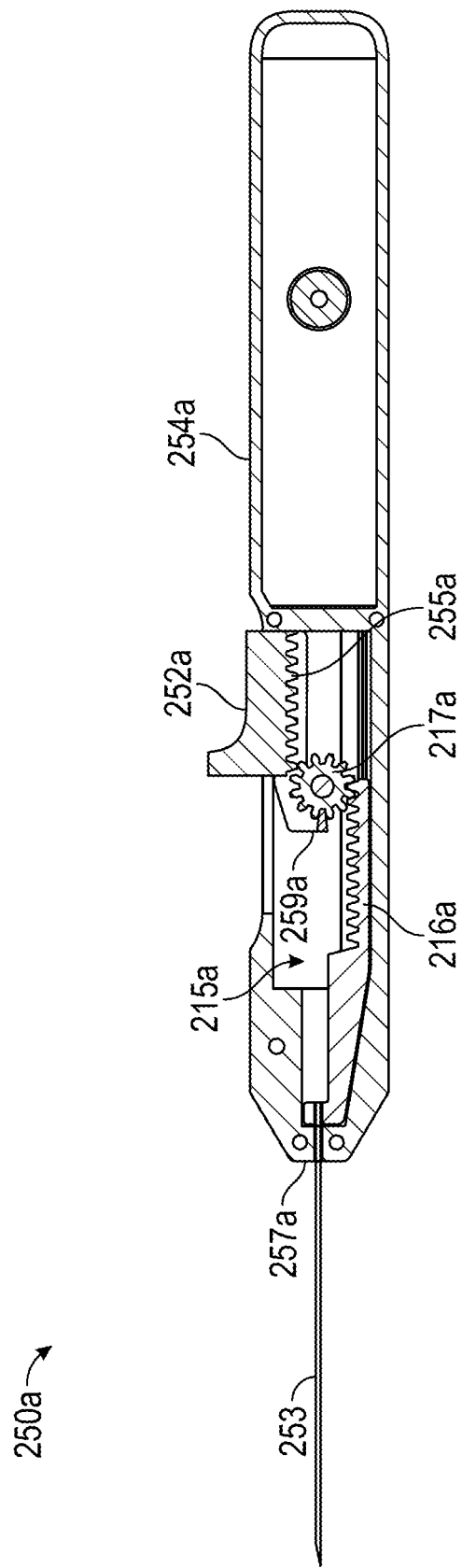
FIG. 30B is a cutaway view of the inserter device of FIG. 30A.

FIGS. 30A and 30B are perspective and cut away views of an inserter device 250a. As shown for example in FIGS. 30A and 30B, the inserter device 250a can include a handle 254a and a needle 253 disposed on or from a nose 257a (e.g., distal end) of the handle 254a. A rack and pinion mechanism 215a can be coupled to the needle 253 and disposed within the handle 254a. The rack and pinion mechanism 215a can, for example, be fixedly attached directly or indirectly to the needle 253 so that the needle 253 moves with the rack and pinion mechanism 215a. The rack and pinion mechanism 215a can include a toothed rack 216a coupled to the needle 253 and also configured to be coupled to or engaged by a gear 217a. An actuator 252a (e.g., slidable button) disposed on the handle 254a can be coupled to or engaged by the gear 217a. As the actuator 252a is pushed forward (e.g., towards the needle 253), actuator teeth 255a can engage the gear 217a and cause the gear to rotate in a first direction (e.g., counterclockwise). Thus, the gear 217a can apply a proximal force to the rack and pinion mechanism 215a, which can in turn retract the needle 253 together with the rack and pinion mechanism 215a. The actuator 252a may also include a gear lock member 259a that prevents the gear 217a from rotating, which can prevent the needle 253 from retracting during insertion of the needle 253 into the eye 101.

Figure 30C:
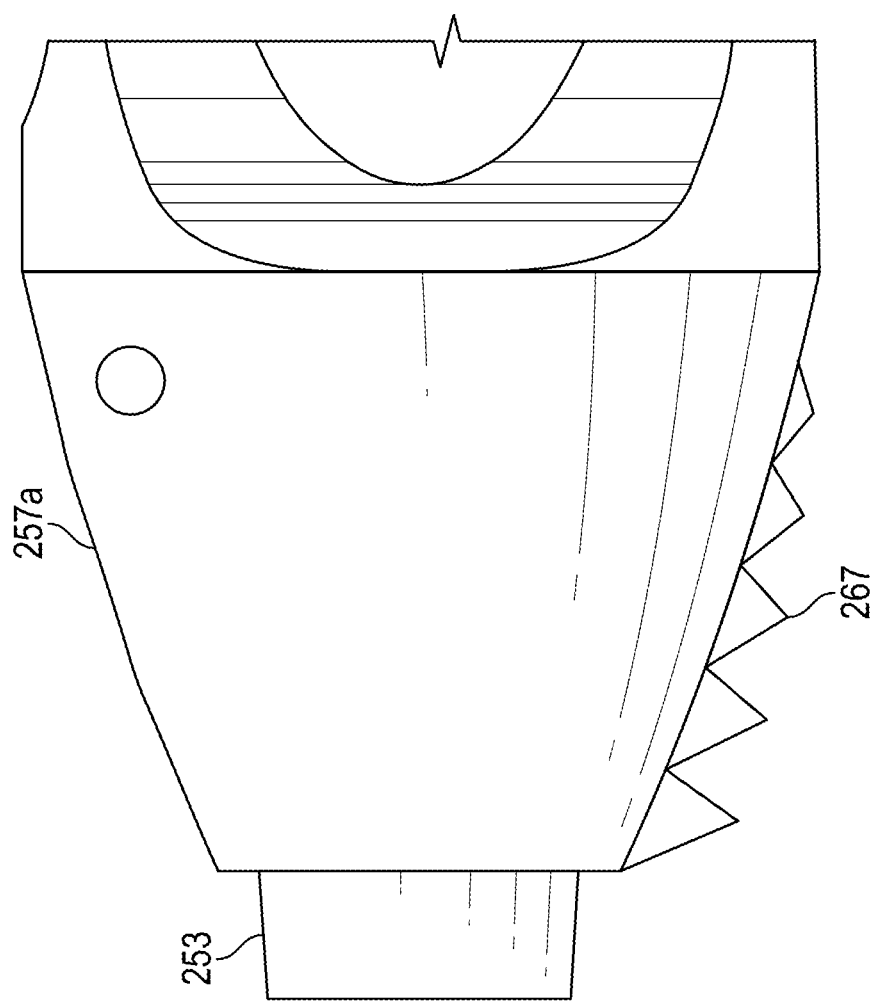
FIG. 30C is a partial top plan view of the inserter device of FIG. 30A with gripping members.

In operation, the needle 253 can be inserted into the eye 101 by a user (e.g., ophthalmic surgeon, robotic arm) grasping the handle 254a and pushing the inserter device 250a to move the needle 253 into an appropriate position within the eye 101, such as when the drainage device 100, 100a, 100b, 100c is correctly positioned in the sclera 113. For example, the needle 253 may be pushed into the eye 101 until the nose 257a reaches or butts up against the surface of the eye 101, thus acting as a natural stop and keeping the eye 101 in place during retraction of the needle 253. As shown in FIG. 30C, the nose 257a may include gripping members 267 (e.g., patterns, materials, protrusions) to further stabilize the inserter device 250a against the eye 101. For example, the gripping members 267 may be configured as teeth or ribs as shown in FIG. 30C. A forward force can then be exerted on the actuator 252a to move the actuator 252a forward, thus disengaging the gear lock member 259a from the gear 217a, engaging the rack and pinion mechanism 215a and retracting the needle 253. Retraction of the needle 253 leaves the drainage device 100, 100a, 100b, 100c positioned within the sclera 113, after which the inserter device 250a can be pulled back, thus removing the needle 253 from the eye 101. Nose 257a may have an external profile having a particular shape, such as a convex profile (e.g., cone shaped as shown in FIG. 30C), a straight profile (e.g., cylindrically shaped), a concave profile (e.g., funnel shaped) and the like. The distal most surface of the nose 257a may be linear as shown in FIG. 30C, convex or concave. For example, a concave profile and/or a concave distal most surface may provide for the nose 257a to conform to or synchronize up with the surface of the eye 101.

Figure 31A:
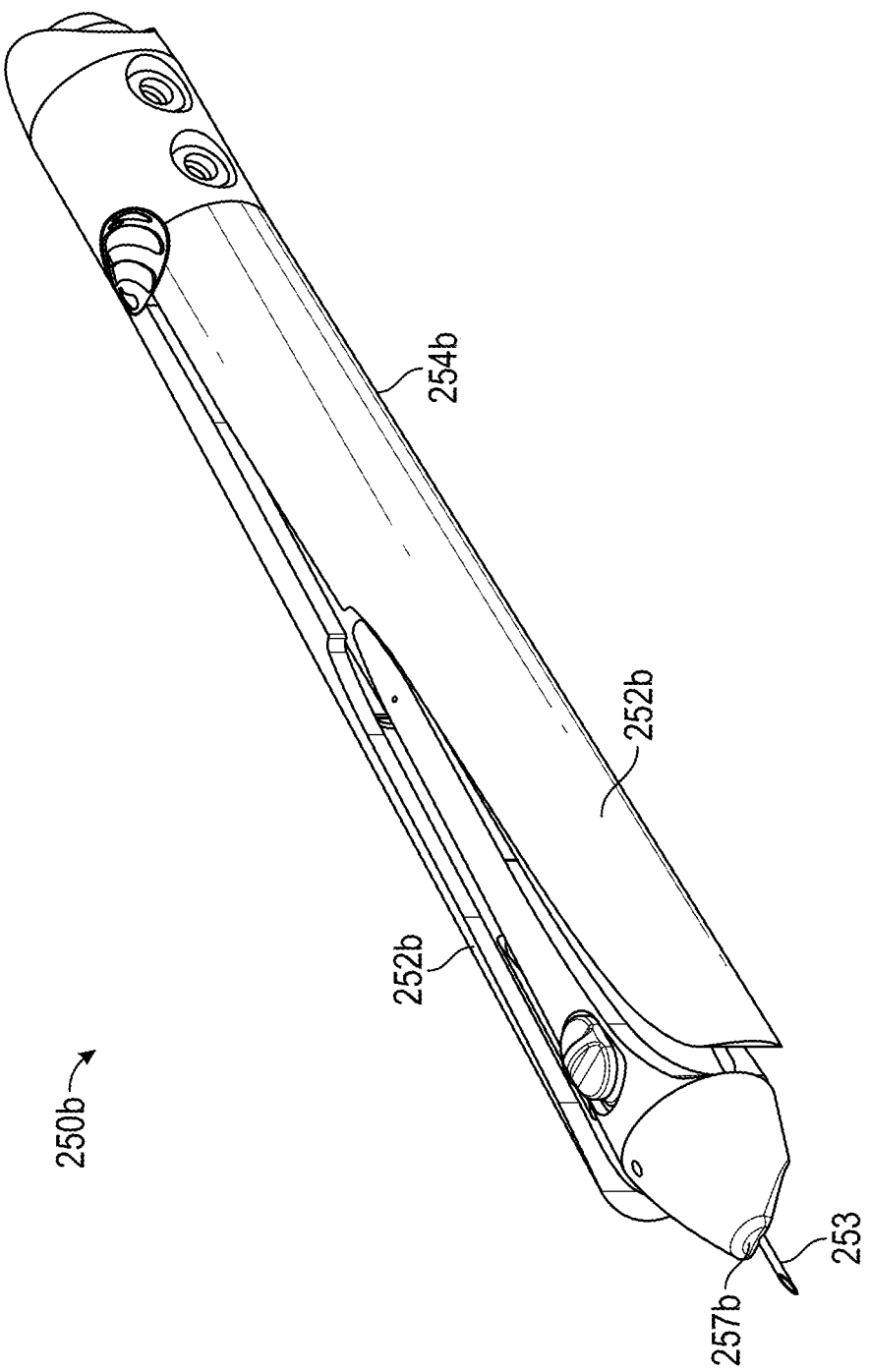
FIG. 31A is a three-dimensional view of an inserter device, in accordance with some embodiments of the present disclosure.
Figure 31B:
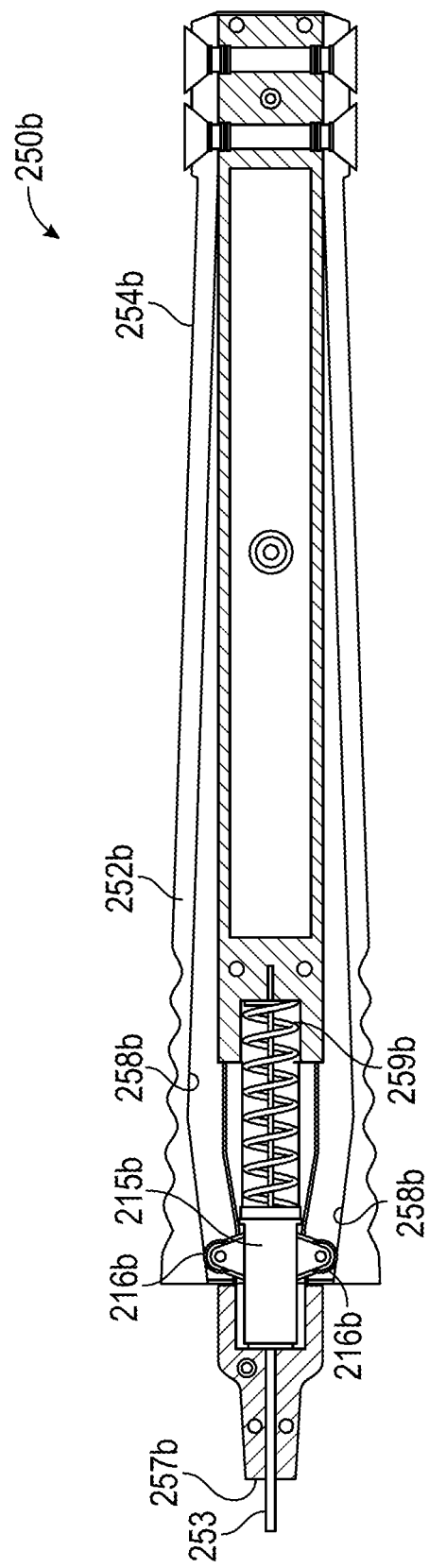
FIG. 31B is a cutaway view of the inserter device of FIG. 31A.

FIGS. 31A and 31B are perspective and cut away views of an inserter device 250b. As shown for example in FIGS. 31A and 31B, the inserter device 250b can include a handle 254b and a needle 253 disposed on or from a nose 257b (e.g., distal end) of the handle 254b. A shuttle mechanism 215b can be coupled to the needle 253 and disposed within the handle 254b. The shuttle mechanism 215b can, for example, be fixedly attached directly or indirectly to the needle 253 so that the needle 253 moves with the shuttle mechanism 215b. The shuttle mechanism 215b can include rollers 216b that are movably coupled to or engaged with ramp features 258b of the handle 254b. The handle 254b can include handle actuators 252b, which can be movable sections of the handle 254b disposed in a clam shell configuration as shown in FIG. 31A. As the handle actuators 252b are moved towards each other (e.g., squeezed together), the rollers 216b travel rearward (e.g., away from the nose 257b) along the ramp features 258b of the handle 254b. Thus, the movement of the rollers 216b can apply a proximal force to the shuttle mechanism 215b, which can in turn retract the needle 253 together with the shuttle mechanism 215b. A spring 259b can be disposed in the handle 254b and configured to bias the shuttle mechanism 215b and thus the needle 253 in the forward position, which can prevent or impede the needle 253 from retracting during insertion of the needle 253 into the eye 101.

Figure 31C:
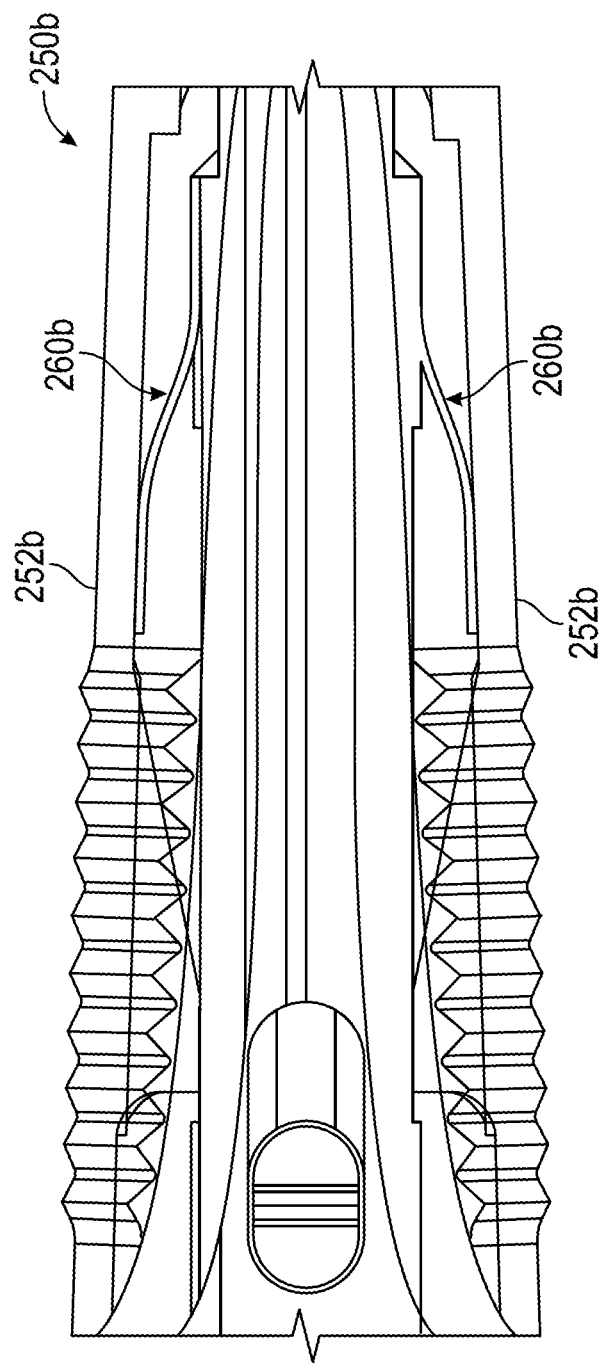
FIG. 31C is a top plan cutaway view of the inserter device of FIG. 31A.

The handle actuators 252b may be formed at least in part with a biasing material (e.g., resistive and/or stiffer material) that is configured to bias the handle actuators 252b outward away from the handle 254b in order to smooth out the squeezing motion required to activate the inserter device 250b and to improve control of the inserter device 250b during use (e.g., when retracting the needle 253 from the eye 101). As shown in FIG. 31C, the inserter device 250b may include biasing members 260b (e.g., springs) configured to bias the handle actuators 252b outward away from the handle 254b. The biasing members 260b may be any type of biasing assembly, such as leaf springs, compression springs, compressible material, and the like. The outward biasing force may be provided by a combination of biasing material and a biasing member 260b.

In operation, the needle 253 can be inserted into the eye 101 by a user (e.g., ophthalmic surgeon, robotic arm) grasping the handle 254b and pushing the inserter device 250b to move the needle 253 into an appropriate position within the eye 101, such as when the drainage device 100, 100a, 100b, 100c is correctly positioned in the sclera 113. For example, the needle 253 may be pushed into the eye 101 until the nose 257b reaches or butts up against the surface of the eye 101, thus acting as a natural stop and keeping the eye 101 in place during retraction of the needle 253. Similarly to nose 257a, nose 257b may include gripping members 267 (e.g., patterns, materials, protrusions) to further stabilize the inserter device 250b against the eye 101. Also, similarly to nose 257a, nose 257b may have an external profile having a particular shape, such as a convex profile (e.g., cone shaped as shown in FIG. 31B), a straight profile (e.g., cylindrically shaped), a concave profile (e.g., funnel shaped) and the like. The distal most surface of the nose 257b may be linear as shown in FIG. 31B, convex or concave. For example, a concave profile and/or a concave distal most surface may provide for the nose 257b to conform to or synchronize up with the surface of the eye 101. A squeezing force can then be exerted on the handle actuators 252b to engage the shuttle mechanism 215b and overcome the biasing force of the spring 259b, thus moving the rollers 216b along the ramp features 258b and retracting the shuttle mechanism 215b and the needle 253. Retraction of the needle 253 leaves the drainage device 100, 100a, 100b, 100c positioned within the sclera 113, after which the inserter device 250b can be pulled back, thus removing the needle 253 from the eye 101. Since the squeezing force on the handle actuators 252b is in a sideways direction (e.g., perpendicular to a longitudinal axis of the handle 254b and the needle 253), displacement or unwanted movement of the drainage device 100, 100a, 100b, 100c can be minimized during retraction of the needle 253.

Figure 32:
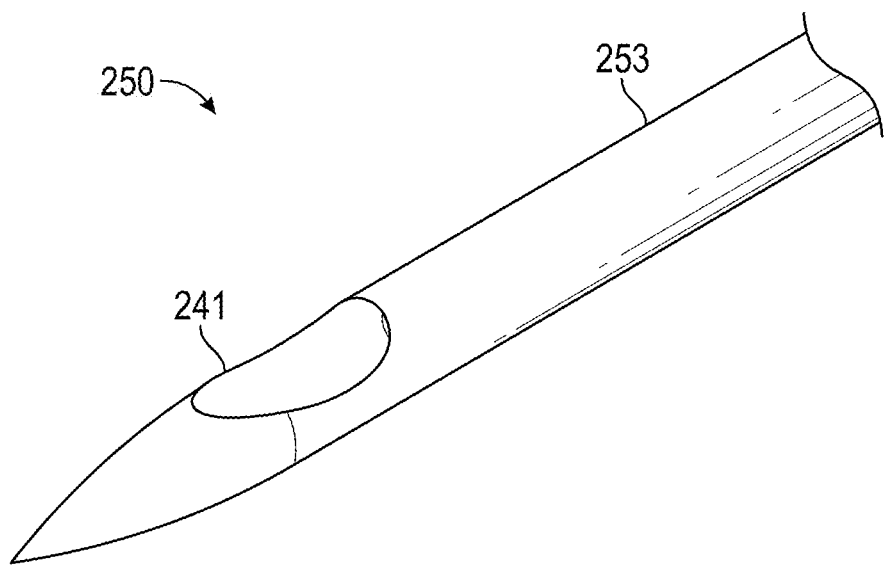
FIG. 32 is a three-dimensional view of an inserter device, in accordance with some embodiments of the present disclosure.
Figure 33:
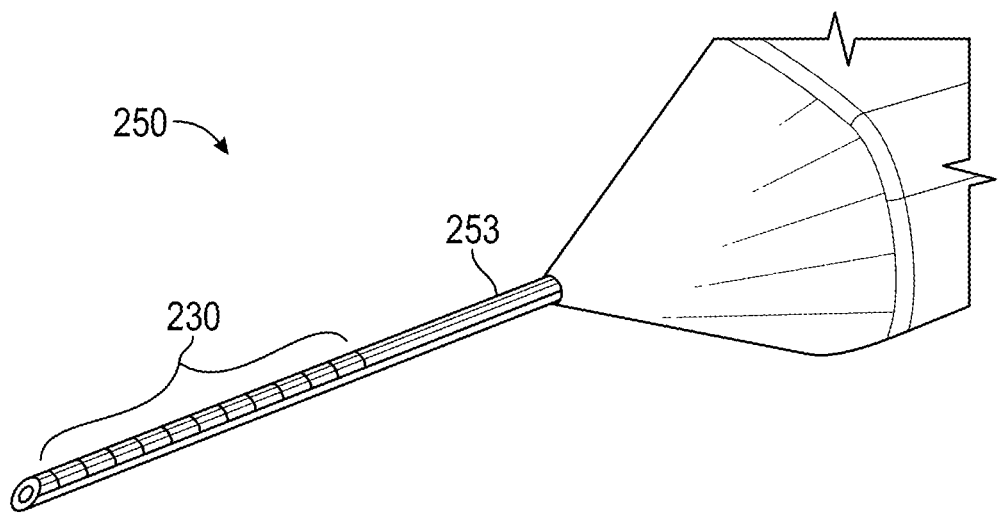
FIG. 33 is a three-dimensional view of an inserter device, in accordance with some embodiments of the present disclosure.

FIGS. 15, 32 and 33 show various examples of needles 253 that can be implemented in the inserter device 250.

According to some embodiments, for example as shown in FIG. 15, a needle 253 can be implemented with one or more slots 201, which can extend proximally and be configured to accommodate one or more corresponding fins 180 of the intraocular drainage device 100. The fins can facilitate retention of the drainage device 100 such as retention of the tube 106 during deployment of the drainage device 100 during an implantation procedure. For example, a stop surface 183 on a proximal side of each fin 180 can abut a distal side of a needle 253 of an inserter device 250 so that the drainage device can remain housed within the needle during distal motion of the needle 253. A ramped surface 184 on a distal side of each fin 180 may facilitate insertion through tissue of the eye during distal motion of the needle 253. The drainage device 100 can be ejected from the inserter device 250 by, for example, retracting the needle 253 while a proximal surface of the first retention member 180 abuts the patient tissue to hold the tube 106 in place in the eye while the needle 253 is retracted. During the implantation procedure, the fin(s) 180 can be disposed in respective slots 201 contained at the distal tip of the needle 253, which may allow for the first retention member 180 to abut the distal side of the needle 253 without having the tube 106 protrude out of the distal end of the needle 253. However, other implementations are contemplated in which the slots 201 are omitted.

According to some embodiments, for example as shown in FIG. 15, the needle 253 can include a beveled distal tip in which the beveled tip has an opening to provide a release port for the drainage device 100.

According to some embodiments, for example as shown in FIG. 32, the needle 253 can be implemented with solid nose distal tip (e.g., with a bullet shape like shown in FIG. 32 or with any other suitable shape). A release port 241 for the drainage device may be disposed on a lateral side of the needle 253 and proximal to the solid nose tip. The solid nose may, for example, help avoid having the needle 253 get clogged with tissue during insertion.

According to some embodiments, for example as shown in FIG. 33, the needle 253 can include an axial marking pattern extending axially along the needle 253 to provide an indication of an insertion depth of the needle 253. For example, the marking pattern can include a series of 1 millimeter graduations, or any other suitable visual marking that that varies axially and is indicative of an insertion depth of the needle 253. As another example, the needle 253 may include at least one measurement marker disposed at a particular distance (e.g., 3 mm) from the tip of the needle.

Figure 34A:
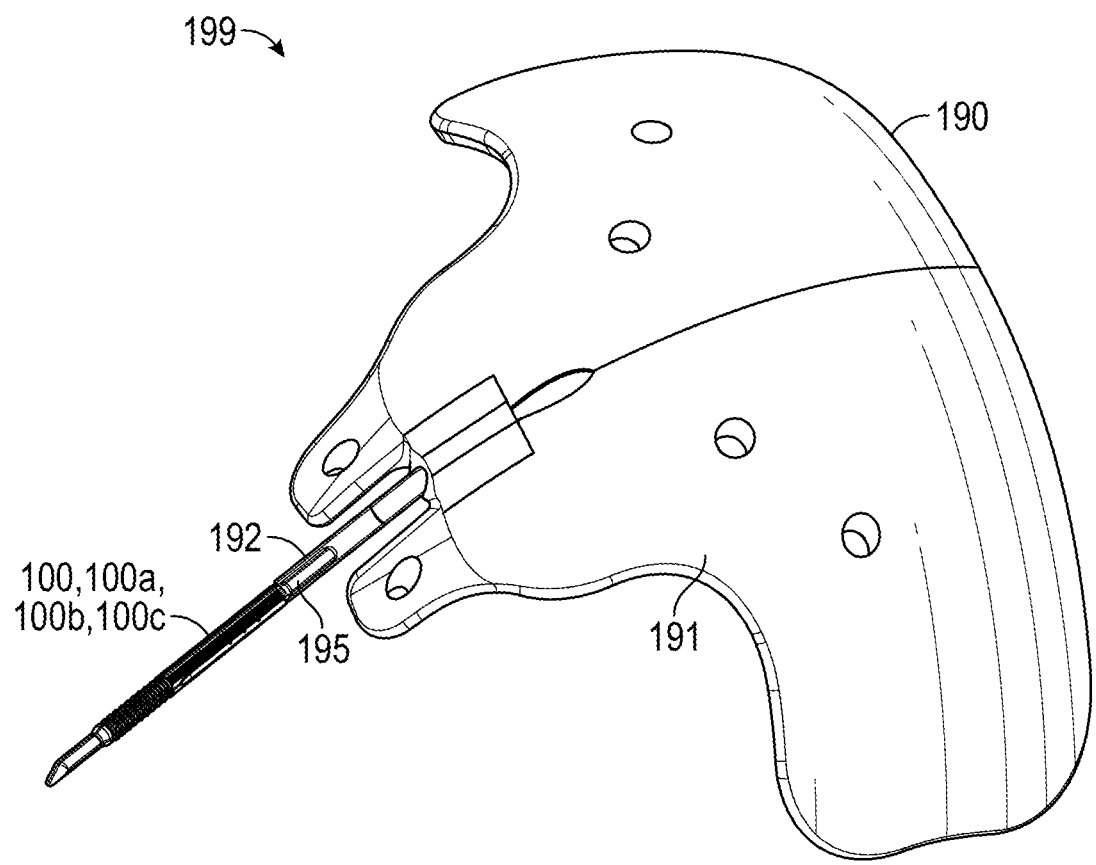
FIG. 34A is a three-dimensional view of an intraocular drainage device assembly in accordance with some embodiments of the present disclosure.
Figure 34B:
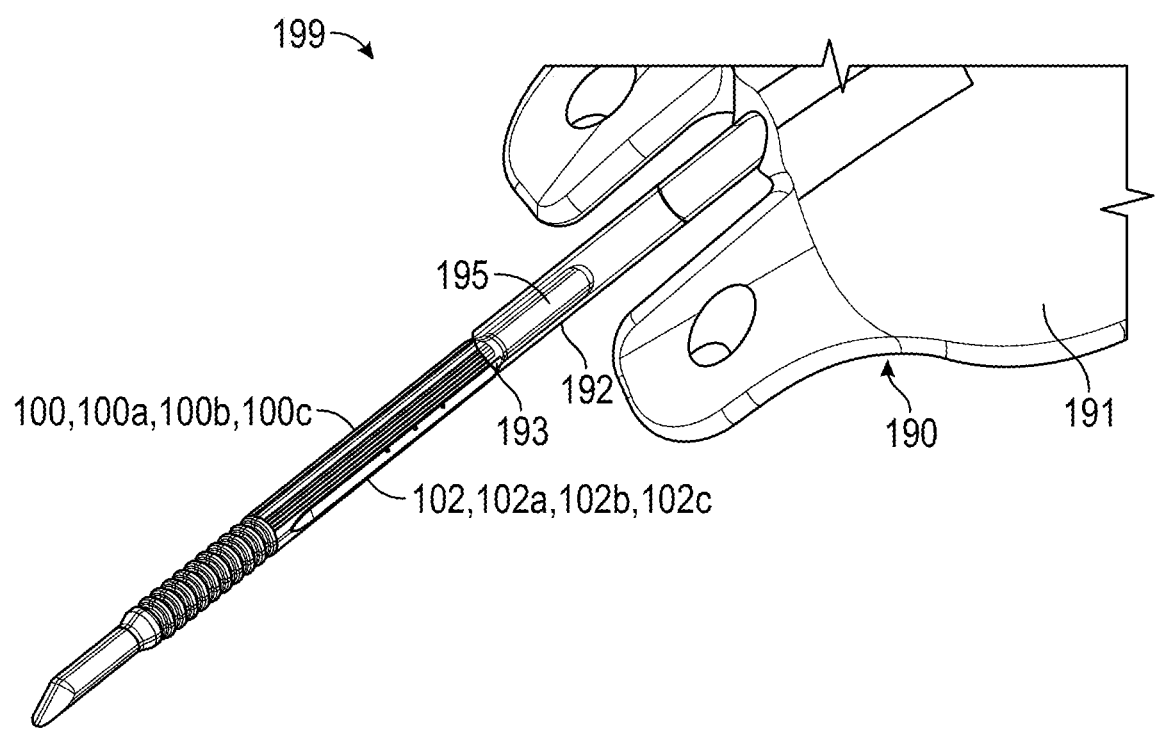
FIG. 34B is a partial three-dimensional view of the intraocular drainage device assembly of FIG. 34A.
Figure 34C:
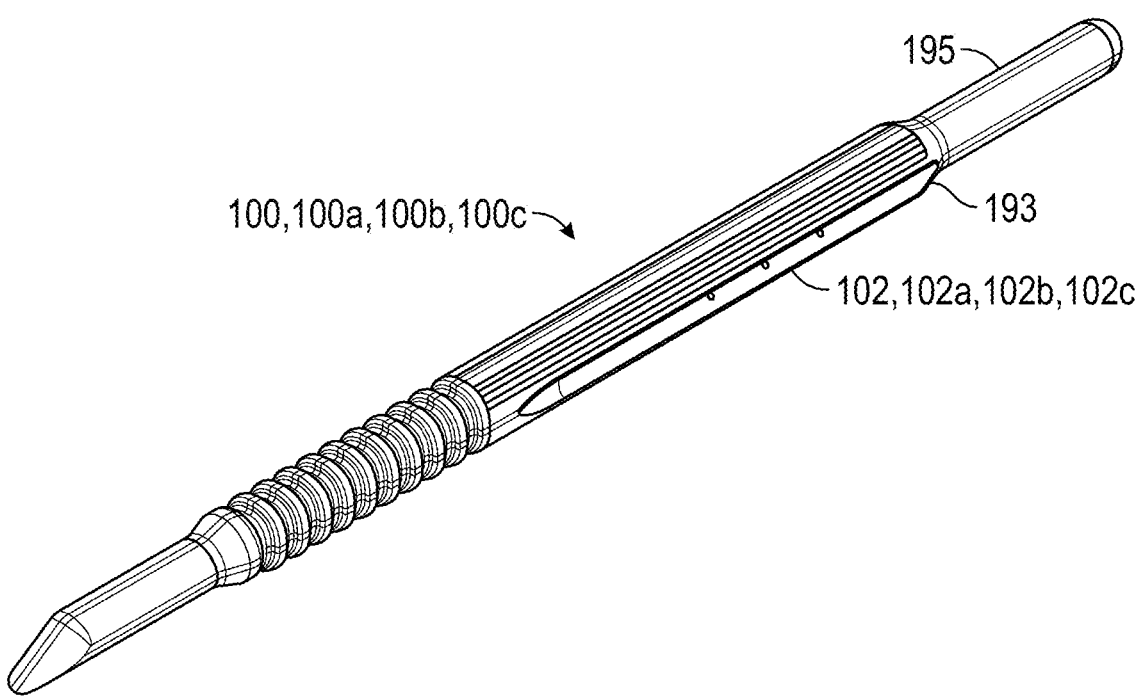
FIG. 34C is a three-dimensional view of a drainage device of the intraocular drainage device assembly of FIG. 34A.

As shown in FIGS. 34A and 34B, an intraocular drainage device assembly 199 can include a plate 190 connected to a drainage device 100, 100a, 100b, 100c. The plate 190 can include a plate member 191 and a tube 192. An adapter 195 can provide an interface to plug the drainage device 100, 100a, 100b, 100c into the tube 192. The adapter 195 can be integrally formed at or coupled to the end of the drainage device body 102, 102a, 102b, 102c, and sized and shaped to sealingly engage or couple with the tube 192. For example, the adapter 195 may have a smooth outer surface (e.g., devoid of patterning) to provide maximum engagement of the adapter 195 outer surface with the internal surface of the tube 192 for proper sealing between the drainage device 100, 100a, 100b, 100c and the plate 190 and/or tube 192. The adapter 195 may be any desired length, such as 2 mm, for example. As shown in FIG. 34C, the adapter 195 may have a stepped down size (e.g., smaller diameter) relative to the drainage device body 102, 102a, 102b, 102c, thus providing a shoulder 193 between the drainage device body 102, 102a, 102b, 102c and the adapter 195. The shoulder 193 can provide a stop in order to prevent over insertion of the drainage device 100, 100a, 100b, 100c into the tube 192.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. Any accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An intraocular drainage device, comprising:
   a tube having a distal end;
   a body disposed proximal to the tube;
   an inlet port disposed on the distal end of the tube and configured to receive an influent fluid from an anterior chamber of an eye;
   an inlet fluid pathway coupled to the inlet port and extending at least partially through the tube;
   an internal port coupled to the inlet fluid pathway and disposed on a proximal end of the tube;
   a plurality of outlet fluid pathways extending at least partially through the body and branching from the inlet fluid pathway;
   a plurality of outlet ports disposed on a distal end of the body and coupled to the plurality of outlet fluid pathways; and
   a distribution chamber between the internal port and the plurality of outlet ports, the distribution chamber formed by at least one of the internal port being recessed in the proximal end of the tube and the plurality of outlet ports being recessed in the distal end of the body.

2. The intraocular drainage device of claim 1, wherein the body is expanded relative to the tube.

3. The intraocular drainage device of claim 1, wherein an outer surface of the body includes a plurality of microgrooves extending longitudinally in a direction substantially parallel to the inlet fluid pathway, and an outer surface of the tube includes a plurality of microgrooves extending circumferentially in a direction substantially perpendicular to the inlet fluid pathway.

4. The intraocular drainage device of claim 1, wherein the tube comprises retention features configured to retain the tube in an implantation site of the eye.

5. The intraocular drainage device of claim 4, wherein the retention features comprise one or more barbs angled towards the body.

6. The intraocular drainage device of claim 4, wherein the retention features comprise a plurality of bumps.

7. The intraocular drainage device of claim 4, wherein the retention features comprise an orifice fitting.

8. The intraocular drainage device of claim 1, wherein the tube comprises a neck region disposed between the body and the distal end of the tube, and wherein the neck region is narrower than the body and the distal end of the tube.

9. The intraocular drainage device of claim 1,
   wherein the drainage device comprises a distal section and a proximal section,
   wherein the inlet fluid pathway is an inlet lumen extending through the distal section,
   wherein the plurality of outlet fluid pathways are a plurality of outlet lumens extending through the proximal section,
   wherein a proximal end of the distal section comprises a first port coupled to the inlet lumen,
   wherein a distal end of the proximal section comprises a plurality of second ports coupled to the plurality of outlet lumens,
   wherein the distal end of the proximal section is joined with the proximal end of the distal section, and
   wherein the distribution chamber is disposed between the first port and the plurality of second ports.

10. The intraocular drainage device of claim 1, wherein the tube and the body are made of a flexible biocompatible material.

11. The intraocular drainage device of claim 1, wherein the tube and the body are made of at least one of a hydrophilic acrylic and a hydrophopic acrylic.

12. The intraocular drainage device of claim 1, wherein the inlet pathway is an inlet lumen extending through an interior of the tube, and wherein the plurality of outlet pathways are a plurality of outlet lumens extending through an interior of the body.

13. The intraocular drainage device of claim 1, wherein the body comprises a plurality of connected polygons, and wherein the plurality of outlet pathways are intervening spaces between the connected polygons.

14. The intraocular drainage device of claim 1, wherein, when implanted in an eye, one or more of the outlet ports are configured to permit fluid flow into a sub-Tenon's space of the eye and one or more others of the outlet ports are configured to permit fluid flow into a subconjunctival space of the eye.

15. The intraocular drainage device of claim 1, wherein an outer surface of the body is coated with a biodegradable material such that the biodegradable material occludes the plurality of outlet ports.

16. A method of making an intraocular drainage device, the method comprising:
   forming a soluble core having a first extending member and a plurality of second extending members branching from the first extending member;
   molding a part around the soluble core; and
   dissolving the soluble core with a solvent to replace the first extending member and the plurality of second extending members with an inlet lumen and a plurality of outlet lumens extending through the molded part.

17. The method of claim 16, further comprising:
   forming the plurality of second extending members at an angle of between 45 degrees and 90 degrees relative to the first extending member.

18. The method of claim 16, wherein the solvent is water and the molded part is made from a material insoluble to water.

* * * * *